(12) United States Patent
Eckhardt et al.

(10) Patent No.: US 7,417,032 B2
(45) Date of Patent: Aug. 26, 2008

(54) D-XYLOPYRANOSYL-PHENYL-SUBSTITUTED CYCLES, MEDICAMENTS CONTAINING SUCH COMPOUNDS, THEIR USE AND PROCESS FOR THEIR MANUFACTURE

(75) Inventors: Matthias Eckhardt, Biberach (DE); Frank Himmelsbach, Mittelbiberach (DE); Peter Eickelmann, Mittelbiberach (DE); Leo Thomas, Biberach (DE); Edward Leon Barsoumian, Toyonaka (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 167 days.

(21) Appl. No.: 11/190,315

(22) Filed: Jul. 27, 2005

(65) Prior Publication Data
US 2006/0025349 A1   Feb. 2, 2006

(30) Foreign Application Priority Data
Jul. 27, 2004 (DE) .................. 10 2004 036 314
Sep. 21, 2004 (DE) .................. 10 2004 046 012

(51) Int. Cl.
*A01N 43/04* (2006.01)
*A61K 31/70* (2006.01)
*C07H 1/00* (2006.01)

(52) U.S. Cl. ................................ 514/23; 536/1.11
(58) Field of Classification Search ............... None
See application file for complete search history.

(56) References Cited

U.S. PATENT DOCUMENTS

| 6,414,126 | B1 | 7/2002 | Ellsworth et al. |
| 6,515,117 | B2 | 2/2003 | Ellsworth et al. |
| 6,774,112 | B2 | 8/2004 | Gougoutas |
| 7,084,124 | B2 | 8/2006 | Patel et al. |
| 7,094,763 | B2 | 8/2006 | Rybczynski et al. |
| 7,094,764 | B2 | 8/2006 | Urbanski et al. |
| 2004/0259819 | A1 | 12/2004 | Frick et al. |
| 2005/0014704 | A1 | 1/2005 | Frick et al. |
| 2005/0124555 | A1 | 6/2005 | Tomiyama et al. |
| 2005/0209166 | A1 | 9/2005 | Eckhardt et al. |
| 2006/0035841 | A1 | 2/2006 | Eckhardt et al. |

FOREIGN PATENT DOCUMENTS

| EP | 1553094 A | 7/2005 |
| WO | WO 98/031697 A1 | 7/1998 |
| WO | WO0127128 A | 4/2001 |
| WO | WO2004013118 A | 2/2004 |
| WO | WO 2004/080990 | * 9/2004 |
| WO | WO2004080990 A | 9/2004 |

OTHER PUBLICATIONS

Accession No. 1987:81540 CAPLUS (Abe et al., "Lignans from *Trachelospermum asiaticum*", Chemical and Pharmaceutical Bulletin, 1986, 34(10), 4340-45).*
Adachi et al., "T-1095, a Renal Na+-Glucose Transport Inhibitor", Metabolism, vol. 49 (8), 2000, 990-995.*

* cited by examiner

*Primary Examiner*—Shaojia Anna Jiang
*Assistant Examiner*—Traviss C. McIntosh, III
(74) *Attorney, Agent, or Firm*—David A. Dow; Mary-Ellen M. Devlin; Michael P. Morris

(57) ABSTRACT

D-Glucopyranosyl-phenyl-substituted cycles of general formula I

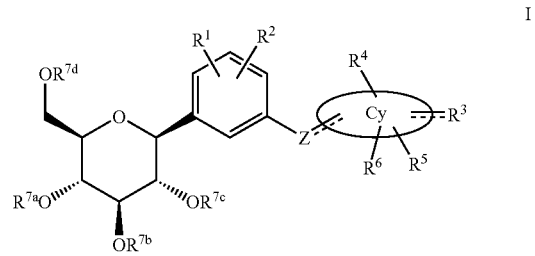

wherein the groups $R^1$ to $R^6$, Z, Cy and $R^{7a}, R^{7b}, R^{7c}, R^{7d}$ are defined as in claim 1, have an inhibiting effect on the sodium-dependent glucose cotransporter SGLT. The present invention also relates to pharmaceutical compositions for the treatment of metabolic disorders.

17 Claims, No Drawings

D-XYLOPYRANOSYL-PHENYL-SUBSTITUTED CYCLES, MEDICAMENTS CONTAINING SUCH COMPOUNDS, THEIR USE AND PROCESS FOR THEIR MANUFACTURE

RELATED APPLICATIONS

This application claims the benefit of DE 102004036314 filed Jul. 27, 2004 and DE 102004046012 filed Sep. 21, 2004 the contents of which are incorporated herein.

THE INVENTION

The present invention relates to D-glucopyranosyl-phenyl-substituted cycles of general formula I

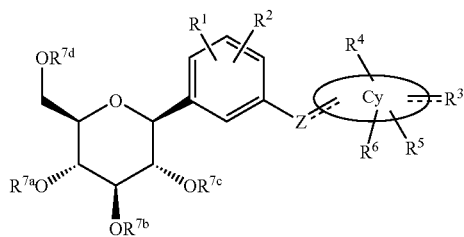

wherein the groups $R^1$ to $R^6$, Z, Cy and $R^{7a}$, $R^{7b}$, $R^{7c}$ and $R^{7d}$ are as hereinafter defined, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. The invention also relates to processes for preparing a pharmaceutical composition and a compound according to the invention.

Compounds which have an inhibitory effect on sodium-dependent glucose cotransporter SGLT are proposed in the literature for the treatment of diseases, particularly diabetes.

Glucopyranosyl-substituted aromatic groups and the preparation thereof and their possible activity as SGLT-2 inhibitors are known from published International Patent Applications WO 98/31697, WO 01/27128, WO 02/083066, WO 03/099836, WO 04/13118, WO 04/80990, WO 04/52902, WO 04/52903 and WO 05/12326.

AIM OF THE INVENTION

The aim of the present invention is to indicate new pyranosyl-substituted phenyls, particularly those which have an effect on sodium-dependent glucose cotransporter SGLT, particularly SGLT2. A further aim of the present invention is to indicate pyranosyl-substituted phenyls which, by comparison with known structurally similar compounds, have a greater inhibitory effect on the sodium-dependent glucose cotransporter SGLT2 in vitro and/or in vivo and/or have improved pharmacological or pharmacokinetic properties.

Moreover the present invention also sets out to prepare new pharmaceutical compositions which are suitable for the prevention and/or treatment of metabolic disorders, particularly diabetes.

The invention also relates to a process for preparing the compounds according to the invention.

Further aims of the present invention will immediately become apparent to the skilled man from the remarks above and hereinafter.

OBJECT OF THE INVENTION

In a first aspect the invention relates to D-glucopyranosyl-phenyl-substituted cycles of general formula I

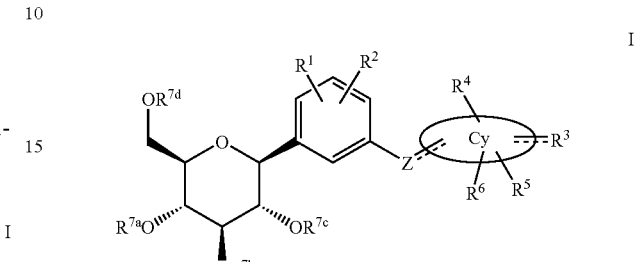

wherein

═ denotes a single or double bond, and

Cy denotes a 5- or 6-membered saturated or monounsaturated carbocycle, which may comprise in the ring one, two or three heteroatoms selected independently of one another from N, O and S, and which is substituted by $R^4$, $R^5$ and $R^6$ through a single bond and by $R^3$ through a single or double bond, and wherein one or two methylene groups may be replaced by CO or a sulphanyl group may be replaced by SO or $SO_2$, and wherein additionally one or more H atoms bound to carbon may be replaced by fluorine, Z denotes —O—, —$CH_2$—, —CH═, —$NR^N$—, —CO—, —S—, —SO— or —$SO_2$—, while H atoms of the methylene or methanylylidene bridge may be substituted independently of one another by $CH_3$ or F;

$R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cyclo-alkyl, $C_{3-10}$-cycloalkyl-$C_{1-3}$-alkyl, $C_{5-10}$-cycloalkenyl, $C_{5-10}$-cyclo-alkenyl-$C_{1-3}$-alkyl, $C_{1-4}$-alkylcarbonyl, arylcarbonyl, heteroarylcarbonyl, aminocarbonyl, $C_{1-4}$-alkylamino-carbonyl, di-($C_{1-3}$-alkyl)aminocarbonyl, pyrrolidin-1-ylcarbonyl, piperidin-1-yl-carbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-10}$-cycloalkyloxy, $C_{5-10}$-cycloalkenyloxy, aryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cycloalkenylsulphanyl, $C_{5-10}$-cycloalkenylsulphinyl, $C_{5-10}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, $C_{1-6}$-alkyl, $C_{2-6}$-alkynyl, $C_{2-6}$-alkenyl, $C_{3-10}$-cycloalkyl, $C_{3-10}$-cycloalkyl-$C_{1-3}$-alkyl, $C_{5-10}$-cycloalkenyl, $C_{5-10}$-cycloalkenyl-$C_{1-3}$-alkyl, aryl, heteroaryl, aryl-$C_{1-3}$-alkyl, heteroaryl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)-aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxyl-carbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkyl-carbonylamino, arylcarbonylamino, heteroarylcarbonylamino, $C_{1-4}$-alkylsulphonyl-amino, arylsulphonylamino, $C_{1-6}$-alkoxy, $C_{3-10}$-cycloalkyloxy, $C_{5-10}$-cycloalkenyloxy, aryloxy, heteroaryloxy, $C_{1-4}$-alkylsulphanyl, $C_{1-4}$-alkylsulphinyl, $C_{1-4}$-alkylsulphonyl, $C_{3-10}$-cycloalkylsulphanyl, $C_{3-10}$-cycloalkylsulphinyl, $C_{3-10}$-cycloalkylsulphonyl, $C_{5-10}$-cyclo-alkenylsulphanyl, $C_{5-10}$-cycloalkenylsulphinyl, $C_{5-10}$-cycloalkenylsulphonyl, arylsulphanyl, arylsulphinyl, arylsulphonyl, amino, hydroxy, cyano or nitro, and alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, or $R^3$ denotes a group Y attached to Cy by a double bond, $R^4$ denotes hydrogen, fluorine, chlorine, cyano, nitro, amino, $C_{1-3}$-alkyl-amino, di-($C_{1-3}$-alkyl)amino, $C_{1-3}$-alkylcarbonylamino, $C_{1-3}$-alkyl, $C_{1-3}$-alkoxy, hydroxycarbonyl, $C_{1-3}$-alkoxycarbonyl or methyl or methoxy substituted by 1 to 3 fluorine atoms, and in the event that $R^3$ and $R^4$ are bound to the same C atom of the Cy ring, $R^3$ and $R^4$ may be joined together such that $R^3$ and $R^4$ together form a $C_{2-6}$-alkylene or $C_{4-6}$-alkenylene bridge, which may be partly or completely fluorinated or may be mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, or in the event that $R^3$ and $R^4$ are bound to two adjacent atoms of the Cy ring, $R^3$ and $R^4$ may be joined together such that $R^3$ and $R^4$ together with the two adjacent atoms of the Cy ring form an anellated saturated or mono- or polyunsaturated 5- or 6-membered carbocycle, wherein one or two methylene groups may be replaced independently of one another by O, S, CO, SO, $SO_2$ or $NR^N$ and/or one or two methyne groups may be replaced by N, and which may be mono- or polyfluorinated or mono- or disubstituted by identical or different substituents selected from chlorine, hydroxy, $C_{1-3}$-alkoxy and $C_{1-3}$-alkyl or in the case of an aromatic anellated ring may be mono- or disubstituted by identical or different substituents L, $R^5$ denotes hydrogen, fluorine, chlorine, cyano, $C_{1-3}$-alkyl, $C_{1-3}$-alkoxy or methyl or methoxy substituted by 1 to 3 fluorine atoms, or $R^4$ and $R^5$ are attached to one another such that $R^4$ and $R^5$ together form a $C_{1-4}$-alkylene or $C_{2-4}$-alkenylene bridge, which together with 2, 3 or 4 atoms of the Cy ring forms an anellated or bridged cycle and which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and $R^6$ denotes hydrogen, $C_{1-3}$-alkyl or fluorine, or $R^4$, $R^5$ and $R^6$ are attached to one another such that $R^4$, $R^5$ and $R^6$ together form a $C_{3-6}$-alkanetriyl bridge, which together with the Cy ring forms a bridged bicyclic or tricyclic system, while the alkanetriyl bridge may be mono- or polyfluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, CO, $SO_2$ or $NR^N$, and Y denotes oxygen, or methylidene, fluoromethylidene, chloromethylidene, $C_{1-6}$-alkyl-methylidene, $C_{2-6}$-alkenyl-methylidene, $C_{2-6}$-alkynyl-methylidene, $C_{3-10}$-cycloalkyl-methylidene, $C_{5-10}$-cycloalkenyl-methylidene, $C_{3-10}$-cycloalkylidene, $C_{5-10}$-cycloalkenylidene, $C_{3-10}$-cycloalkyl-$C_{1-3}$-alkyl-methylidene, $C_{5-10}$-cycloalkenyl-$C_{1-3}$-alkyl-methylidene, arylmethylidene, heteroaryl-methylidene, aryl-$C_{1-3}$-alkyl-methylidene or heteroaryl-$C_{1-3}$-alkyl-methylidene, while alkyl, alkenyl, alkynyl, cycloalkyl, cycloalkenyl, cycloalkylidene and cycloalkenylidene groups may be partly or completely fluorinated or mono- or disubstituted by identical or different substituents selected from chlorine, cyano, hydroxy, $C_{1-3}$-alkoxy, $C_{1-3}$-alkylsulphanyl and $C_{1-3}$-alkyl, and the above-mentioned unsubstituted methylidene group or the above-mentioned monosubstituted methylidene groups may additionally be monosubstituted by fluorine, chlorine, $C_{1-3}$-alkyl, trifluoromethyl, $C_{1-4}$-alkoxy, cyano or nitro, and in cycloalkyl, cycloalkenyl, cycloalkylidene and cycloalkenylidene groups one or two methylene groups may be replaced independently of one another by O, S, CO, SO, $SO_2$ or $NR^N$, or Y denotes a group according to partial formula

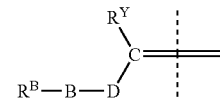

wherein

D denotes carbonyl or sulphonyl, $R^Y$ denotes hydrogen, fluorine, chlorine, cyano, trifluoromethyl or $C_{1-3}$-alkyl, B denotes a single bond, —O— or —NR$^N$—, $R^B$ denotes hydrogen, $C_{1-6}$-alkyl, $C_{3-6}$-alkenyl, $C_{3-6}$-alkynyl, $C_{3-10}$-cycloalkyl, $C_{5-10}$-cycloalkenyl, $C_{3-10}$-cycloalkyl-$C_{1-3}$-alkyl, $C_{5-10}$-cycloalkenyl-$C_{1-3}$-alkyl, aryl, heteroaryl, aryl-$C_{1-3}$-alkyl or heteroaryl-$C_{1-3}$-alkyl, while alkyl, cycloalkyl and cycloalkenyl groups may be partly or completely fluorinated or may be mono- or disubstituted by identical or different substituents selected from chlorine, cyano, hydroxy, $C_{1-3}$-alkoxy and $C_{1-3}$-alkyl, or $R^B$ and B are joined together to form a heterocyclic ring selected from pyrrolidine, morpholine, piperidine, piperazine and 4-($C_{1-4}$-alkyl)-piperazine, while the heterocyclic ring is bound to the group D via the imino group, $R^N$ independently of one another denote H or $C_{1-4}$-alkyl, L selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$, $R^{7d}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while by the aryl groups mentioned in the definition of the above groups is meant phenyl or naphthyl groups, which may be mono- or disubstituted independently of one another by identical or different groups L; and by the heteroaryl groups mentioned in the definition of the above-mentioned groups is meant a pyrrolyl, furanyl, thienyl, imidazolyl, pyridyl, indolyl, benzofuranyl, benzothiophenyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted independently of one another by identical or different groups L;

while by the N-heterocycloalkyl group mentioned in the definition of the above-mentioned groups is meant a saturated carbocyclic ring which comprises an imino group in the ring, which may comprise another optionally substituted imino group or an O or S atom in the ring, and unless otherwise stated, the above-mentioned alkyl groups may be straight-chain or branched, the tautomers, their stereoisomers, the mixtures thereof and the salts thereof, particularly the physiologically acceptable salts thereof, but excluding the following compound (D1):

(D1) 3-[(3-β-D-glucopyranosyl-4,5-dimethoxyphenyl)methyl]-4-[(3,4-dimethoxyphenyl)methyl]-dihydro-2(3H)-furanone.

The compounds of general formula I according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

The compound (D1) 3-[(3-β-D-glucopyranosyl-4,5-dimethoxyphenyl)methyl]-4-[(3,4-dimethoxyphenyl)methyl]-dihydro-2(3H)-furanone (Chemical Abstracts Registry No. 106678-86-8) is mentioned in Abe, Fumiko; Yamauchi, Tatsuo; Lignans from Trachelospermum asiaticum, Chemical & Pharmaceutical Bulletin (1986), 34 (19), 4340-5, but without any mention of a connection to an inhibiting effect on SGLT.

Therefore, the invention also relates to the use of the compounds according to the invention, including the physiologically acceptable salts, including the compound (D1) explicitly excluded hereinbefore or one of the physiologically acceptable salts thereof, as pharmaceutical compositions.

This invention also relates to pharmaceutical compositions, containing at least one compound according to the invention or a physiologically acceptable salt according to the invention, including the compound (D1) explicitly excluded hereinbefore or one of the physiologically acceptable salts thereof, optionally together with one or more inert carriers and/or diluents.

A further subject of this invention is the use of at least one compound according to the invention or a physiologically acceptable salt of such a compound, including the compound (D1) explicitly excluded hereinbefore or one of the physiologically acceptable salts thereof, for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention or a physiologically acceptable salt of such a compound, including the compound (D1) explicitly excluded hereinbefore or one of the physiologically acceptable salts thereof, for preparing a pharmaceutical composition which is suitable for the treatment of metabolic disorders.

This invention also relates to the use of at least one compound according to the invention or one of the physiologically acceptable salts thereof, including the compound (D1) explicitly excluded hereinbefore or one of the physiologically acceptable salts thereof, for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention or one of the physiologically acceptable salts thereof, including the compound (D1) explicitly excluded hereinbefore or one of the physiologically acceptable salts thereof, is incorporated in one or more inert carriers and/or diluents by a non-chemical method.

The present invention also relates to a process for preparing the compounds of general formula I according to the invention, characterised in that a) in order to prepare compounds of general formula I as defined hereinbefore and hereinafter, a compound of general formula II

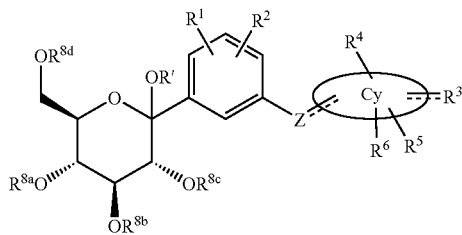

wherein
R' denotes H, $C_{1-4}$-alkyl, ($C_{1-18}$-alkyl)carbonyl, ($C_{1-18}$-alkyl)oxycarbonyl, arylcarbonyl or aryl-($C_{1-3}$-alkyl)-carbonyl, wherein the alkyl or aryl groups may be mono- or polysubstituted by halogen;
$R^{8a}$, $R^{8b}$, $R^{8c}$, $R^{8d}$ independently of one another have one of the meanings given hereinbefore and hereinafter for the groups $R^{7a}$, $R^{7b}$, $R^{7c}$, $R^{7d}$, or denote a benzyl group or a $R^aR^bR^cSi$ group or a ketal or acetal group, particularly an alkylidene or arylalkylidene ketal or acetal group, while in each case two adjacent groups $R^{8a}$, $R^{8b}$, $R^{8c}$, $R^{8d}$ may form a cyclic ketal or acetal group or a 1,2-di($C_{1-3}$-alkoxy)-1,2-di($C_{1-3}$-alkyl)-ethylene bridge, while the above-mentioned ethylene bridge together with two oxygen atoms and the two associated carbon atoms of the pyranose ring form a substituted dioxane ring, particularly a 2,3-dimethyl-2,3-di($C_{1-3}$-alkoxy)-1,4-dioxan ring, and alkyl, aryl and/or benzyl groups may be mono- or polysubstituted by halogen or $C_{1-3}$-alkoxy and benzyl groups may also be substituted by a di-($C_{1-3}$-alkyl)amino group; and
$R^a$, $R^b$, $R^c$ independently of one another represent $C_{1-4}$-alkyl, aryl or aryl-$C_{1-3}$-alkyl, wherein the aryl or alkyl groups may be mono- or polysubstituted by halogen;

while by the aryl groups mentioned in the definition of the above groups are meant phenyl or naphthyl groups, preferably phenyl groups;

and wherein the groups $R^1$ to $R^6$ and the bridge Z and the ring Cy are defined as hereinbefore and hereinafter;

is reacted with a reducing agent in the presence of an acid, and any protective groups present are cleaved simultaneously or thereafter; or b) in order to prepare compounds of general formula I wherein $R^{7a}$, $R^b$, $R^{7c}$ and $R^{7d}$ denote hydrogen,
in a compound of general formula III

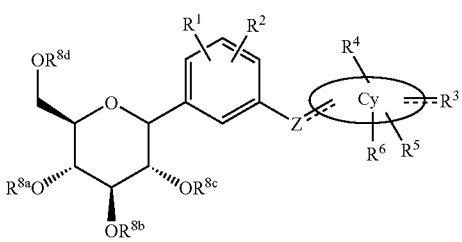

wherein Z, Cy, $R^{8a}$, $R^{8b}$, $R^{8c}$, $R^{8d}$ as well as $R^1$ to $R^6$ are defined as hereinbefore and hereinafter, and at least one of the groups $R^{8a}$, $R^{8b}$, $R^{8c}$ and $R^{8d}$ does not represent hydrogen, the groups $R^{8a}$, $R^{8b}$, $R^{8c}$ or $R^{8d}$ which do not represent hydrogen are removed, particularly hydrolysed; and if necessary any protecting group used in process a) or b) in the reactions described above is cleaved and/or if desired a compound of general formula I thus obtained is selectively derivatised at a hydroxy group or this is substituted and/or if desired a compound of general formula I thus obtained is resolved into its stereoisomers and/or if desired a compound of general formula I thus obtained is converted into the salts thereof, particularly for pharmaceutical use into the physiologically acceptable salts thereof.

DETAILED DESCRIPTION OF THE INVENTION

Unless otherwise stated the groups, residues and substituents, particularly $R^1$ to $R^6$, Y, Z, Cy, L, $R^N$, $R^{7a}$, $R^{7b}$, $R^{7c}$, $R^{7d}$, $R^Y$, D, B, $R^B$, are defined as above and hereinafter.

If residues, substituents or groups occur several times in a compound, they may have the same or different meanings.

The term aryl used above and hereinafter, for example in the groups Y, $R^1$ and $R^3$, preferably denotes phenyl. According to the general definition and unless otherwise stated, the aryl group, particularly the phenyl group, may be mono- or disubstituted by identical or different groups L.

The term heteroaryl used above and hereinafter, for example in the groups Y, $R^1$ and $R^3$, preferably denotes pyridinyl, pyrimidinyl, pyridazinyl, pyrazinyl, triazinyl, imidazolyl, pyrazolyl, triazolyl, tetrazolyl, oxazolyl, oxadiazolyl, thiazolyl or thiadiazolyl. According to the general definition and unless otherwise stated, the heteroaryl group may be mono- or disubstituted by identical or different groups L.

Preferred meanings of the Cy ring are cyclopentane, cyclohexane, pyrrolidine, piperidine, piperazine, morpholine, tetrahydrofuran, tetrahydropyran, 1,3-dioxane, 1,4-dioxane, tetrahydrothiophene, dithiolane and 1,3-dithiane, wherein a methylene group may be replaced by CO, and which are substituted as specified above with $R^3$, $R^4$, $R^5$ and $R^6$, and wherein one or more H atoms bound to carbon may be replaced by fluorine.

If in the above-mentioned cyclic groups a methylene group is replaced by CO, preferred definitions of the group Cy are selected from tetrahydrofuranone, tetrahydropyranone, piperidinone, piperazinone and morpholinone.

Moreover, in the groups specified hereinbefore as being preferred for Cy, a double bond may be present in each case. Preferred meanings of such monounsaturated Cy cycles are cyclopentene and cyclohexene. If any substituents $R^3$, $R^4$, $R^5$ and/or $R^6$ are joined together, this double bond may also be part of an anellated cyclic system.

Particularly preferred meanings of the Cy ring are cyclopentane, cyclohexane, pyrrolidine, piperidine, piperazine, tetrahydrofuran and 1,3-dioxane, which are substituted as specified above with $R^3$, $R^4$, $R^5$ and $R^6$, and wherein one or more H atoms bound to carbon may be replaced by fluorine.

The compounds of formula I according to the invention may be divided into two embodiments according to the number of ring atoms in the Cy ring.

According to a first embodiment preferred compounds of formula I according to the invention are those wherein the group Cy denotes a 6-membered saturated or monounsaturated carbocycle, which may comprise in the ring one, two or three, preferably one or two heteroatoms selected independently of one another from N, O and S, and which is substituted by $R^4$, $R^5$ and $R^6$ through a single bond and by $R^3$ through a single or double bond, and wherein a methylene group may be replaced by CO or a sulphanyl group may be replaced by SO or $SO_2$, and wherein one or more H atoms bound to carbon may be replaced by fluorine, and wherein the other substituents and groups have the meanings given hereinbefore and hereinafter.

Preferred Cy rings according to this embodiment are cyclohexane, piperidine, piperazine, morpholine, tetrahydropyran, 1,3-dioxane, 1,4-dioxane and 1,3-dithiane, wherein a methylene group may be replaced by CO, and which are substituted as specified hereinbefore by $R^3$, $R^4$, $R^5$ and $R^6$, and wherein one or more H atoms bound to carbon may be replaced by fluorine.

If in the above-mentioned cyclic groups a methylene group is replaced by CO, preferred definitions of the group Cy are selected from tetrahydropyranone, piperidinone, piperazinone and morpholinone.

Moreover a double bond may be present in each case in the groups specified as being preferred for Cy. A preferred definition of such monounsaturated Cy rings is cyclohexene. If substituents $R^3$, $R^4$, $R^5$ and/or $R^6$ are joined together, this double bond may also be part of an anellated cyclic system.

Particularly preferred Cy are cyclohexane, cyclohexene, piperidine, piperazine and 1,3-dioxane, which are substituted by $R^3$, $R^4$, $R^5$ and $R^6$ as stated hereinbefore, and wherein one or more H atoms bound to carbon may be replaced by fluorine.

According to a second embodiment preferred compounds of formula I according to the invention are those wherein the group Cy denotes a 5-membered saturated or monounsaturated carbocycle, which may comprise in the ring one, two or three, preferably one or two heteroatoms selected independently of one another from N, O and S, and which is substituted by $R^4$, $R^5$ and $R^6$ through a single bond and by $R^3$ through a single or double bond, and wherein a methylene group may be replaced by CO or a sulphanyl group may be replaced by SO or $SO_2$, and wherein one or more H atoms bound to carbon may be replaced by fluorine, and wherein the remaining substituents and groups have the meanings given hereinbefore and hereinafter.

According to this embodiment preferred cycles Cy are cyclopentane, pyrrolidine, tetrahydrofuran, dithiolane and tetrahydrothiophene, wherein a methylene group may be replaced by CO, and which are substituted by $R^3$, $R^4$, $R^5$ and $R^6$ as stated hereinbefore, and wherein one or more H atoms bound to carbon may be replaced by fluorine.

If in the above-mentioned cyclic groups a methylene group is replaced by CO, a preferred definition of the group Cy is tetrahydrofuranone.

Moreover in the groups specified hereinbefore as being preferred for Cy, a double bond may be present in each case. A preferred meaning of such monounsaturated cycles Cy is cyclopentene. If substituents $R^3$, $R^4$, $R^5$ and/or $R^6$ are joined together, this double bond may also be part of an anellated cyclic system.

Particularly preferred Cy are cyclopentane, pyrrolidine and tetrahydrofuran, which are substituted as stated hereinbefore with $R^3$, $R^4$, $R^5$ and $R^6$, and wherein one or more H atoms bound to carbon may be replaced by fluorine.

In the event that Cy denotes a 6-membered cyclic group, the group $R^3$ is preferably in the 3- or 4-position to the bridge Z, particularly preferably in the 4-position to the bridge Z.

In the event that Cy denotes a 5-membered cycle group, the group $R^3$ is preferably in the 3-position to the bridge Z.

Therefore, preferred compounds according to the first embodiment, wherein Cy denotes a 6-membered cyclic group, are described by formulae I.1 and I.1':

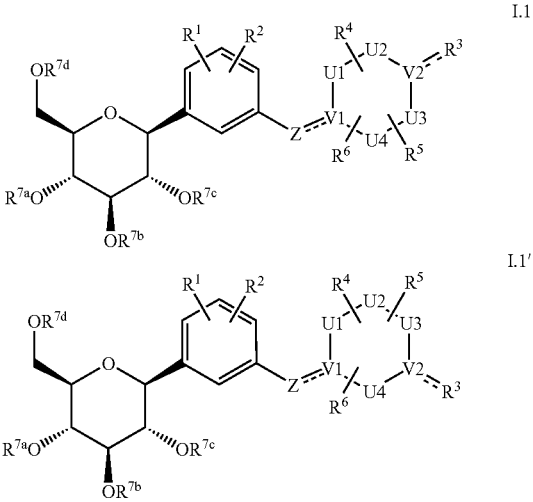

wherein

V1, V2 independently of one another represent C or N,

U1, U2,

U3, U4 independently of one another represent C, N, O, CO or $SO_2$, with the proviso that in the ring formed by U and V there are a maximum of 2 heteroatoms selected from N and O, which are not directly joined together, and there is at most one group selected from CO and $SO_2$, and remaining free chemical bonds to C and N atoms are saturated with hydrogen; and wherein the remaining groups and substituents have one of the meanings given hereinbefore or hereinafter.

Moreover preferred compounds according to the second embodiment, wherein Cy denotes a 5-membered cyclic group, may be described by formula I.2:

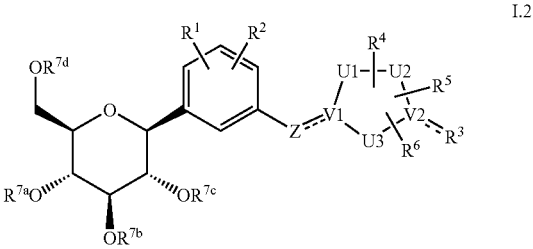

wherein

V1, V2 independently of one another represent C or N,

U1, U2,

U3 independently of one another represent C, N, O, CO or $SO_2$, with the proviso that in the ring formed by U and V there are a maximum of 2 heteroatoms selected from N and O, which are not directly joined together, and there is a maximum of one group selected from CO and $SO_2$, and remaining free chemical bonds to C and N atoms are saturated with hydrogen; and wherein the remaining groups and substituents have one of the meanings given hereinbefore or hereinafter.

Some preferred definitions of the remaining groups and substituents in the novel compounds of general formula I, particularly of formulae I.1, I.1' and I.2, will now be given:

Preferably $R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{5-10}$-cycloalkenyl, $C_{1-4}$-alkylcarbonyl, aminocarbonyl, $C_{1-4}$-alkyl-aminocarbonyl, di-($C_{1-3}$-alkyl)aminocarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, $C_{1-4}$-alkylcarbonylamino, $C_{1-6}$-alkyloxy, $C_{3-10}$-cycloalkyloxy, $C_{5-10}$-cycloalkenyloxy, $C_{1-4}$-alkylsulphanyl, $C_{1-4}$-alkylsulphonyl, $C_{3-10}$-cycloalkylsulphanyl, $C_{3-10}$-cycloalkylsulphonyl, $C_{5-10}$-cycloalkenylsulphanyl, $C_{5-10}$-cycloalkenyl-sulphonyl, hydroxy and cyano, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and while in cycloalkyl- and cycloalkenyl groups one or two methylene groups may be replaced independently of one another by O, S, CO, SO or $SO_2$, and in N-heterocycloalkyl groups a methylene group may be replaced by CO or $SO_2$.

If the group $R^1$ denotes a cycloalkyl or cycloalkenyl group, wherein one or two methylene groups are replaced independently of one another by O, S, CO, SO or $SO_2$, preferred meanings of the group $R^1$ are selected from among tetrahydrofuranyl, tetrahydrofuranonyl, tetrahydrothienyl, tetrahydropyranyl, tetrahydropyranonyl, dioxanyl and trioxanyl.

If the group $R^1$ denotes an N-heterocycloalkyl group wherein a methylene group is replaced by CO or $SO_2$, preferred meanings of the group $R^1$ are selected from among pyrrolidinone, piperidinone, piperazinone and morpholinone.

Particularly preferably $R^1$ denotes hydrogen, fluorine, chlorine, bromine, iodine, $C_{1-6}$-alkyl, $C_{2-6}$-alkynyl, $C_{2-6}$-alkenyl, $C_{3-10}$-cycloalkyl, $C_{5-10}$-cycloalkenyl, $C_{1-6}$-alkyloxy, $C_{3-10}$-cycloalkyloxy or cyano, while in cycloalkyl and cycloalkenyl groups one or two methylene units may be replaced independently of one another by O or CO and alkyl, alkenyl and alkynyl groups may be partly or completely fluorinated.

Examples of the most particularly preferred groups $R^1$ are hydrogen, fluorine, chlorine, bromine, methyl, ethyl, isopropyl, trifluoromethyl, ethynyl, methoxy, cyclopentyloxy and cyano, particularly chlorine and methyl.

Preferred meanings of the group $R^2$ are hydrogen, fluorine, chlorine, bromine, methyl, hydroxy, methoxy, ethoxy, trifluoromethoxy, cyano, nitro and methyl substituted by 1 to 3 fluorine atoms.

Particularly preferred meanings of the group $R^2$ are hydrogen, fluorine, hydroxy, methoxy, ethoxy and methyl, particularly hydrogen and methyl.

In the event that $R^1$ and $R^2$ are bound to two adjacent C atoms of the phenyl ring, $R^1$ and $R^2$ may be joined together such that $R^1$ and $R^2$ together preferably form a $C_{3-4}$-alkylene or butadienylene bridge, wherein one or two methylene units may be replaced independently of one another by O, $NR^N$ or CO, and wherein in the case of a butadienylene bridge a methyne group may be replaced by an N atom. Preferably the groups $R^1$ and $R^2$ joined together form, with the phenyl ring to which they are attached, a bicyclic ring system selected from indane, dihydroindole, dihydrobenzofuran, tetrahydroquinoline, dihydro-quinolinone, tetrahydroisoquinoline, dihydroisoquinolinone, tetrahydronaphthalene, naphthalene, quinoline or isoquinoline.

The substituent $R^3$ has the meanings given hereinbefore. In the event that $R^3$ is bound to an N atom, $R^3$ preferably does not denote halogen or alkyl, cycloalkyl, cycloalkenyl or arylsulphanyl.

If the group $R^3$ is bound to Cy through a single bond, particularly to a C atom, $R^3$ preferably denotes hydrogen, fluorine, chlorine, $C_{1-6}$alkyl, $C_{2-6}$-alkynyl, $C_{2-6}$-alkenyl, $C_{3-10}$-cycloalkyl, $C_{3-10}$-cycloalkyl-methyl, $C_{5-10}$-cycloalkenyl, $C_{3-10}$-cycloalkenyl-methyl, aryl, heteroaryl, $C_{1-4}$-alkylcarbonyl, aminocarbonyl, $C_{1-4}$-alkylaminocarbonyl, di-($C_{1-3}$-alkyl)aminocarbonyl, $C_{1-4}$-alkoxycarbonyl, di-($C_{1-3}$-alkyl)amino, pyrrolidin-1-yl, piperidin-1-yl, morpholin-4-yl, $C_{1-4}$-alkylcarbonylamino, $C_{1-6}$-alkoxy, $C_{3-10}$-cycloalkyloxy, $C_{5-10}$-cycloalkenyl-oxy, aryloxy, heteroaryloxy, $C_{1-4}$-alkylsulphanyl, $C_{1-4}$-alkylsulphonyl, $C_{3-10}$-cycloalkylsulphanyl, $C_{3-10}$-cyclo-alkylsulphonyl, $C_{5-10}$-cycloalkenylsulphanyl, $C_{5-10}$-cycloalkenylsulphonyl, hydroxy and cyano, and in the event that $R^3$ is bound to an N atom, $R^3$ preferably denotes hydrogen, cyano, $C_{1-4}$-alkyl, $C_{2-6}$-alkynyl, $C_{2-6}$-alkenyl, $C_{3-6}$-cycloalkyl, $C_{3-6}$-cycloalkyl-$C_{1-3}$-alkyl, $C_{5-6}$-cycloalkenyl, $C_{5-6}$-cycloalkenyl-$C_{1-3}$-alkyl, aryl, heteroaryl, aryl-$C_{1-3}$-alkyl, heteroaryl-$C_{1-3}$-alkyl, $C_{1-4}$-alkylcarbonyl, arylcarbonyl, heteroarylcarbonyl, $C_{1-4}$-alkylsulphonyl, arylsulphonyl or heteroarylsulphonyl, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, while the terms aryl and heteroaryl are as hereinbefore defined and aryl and heteroaryl groups may independently of one another be mono- or disubstituted by identical or different groups L.

If the group $R^3$ denotes a cycloalkyl or cycloalkenyl group, wherein one or two methylene groups are replaced independently of one another by O, S, CO, SO or $SO_2$, preferred definitions of the group $R^3$ are selected from among tetrahydrofuranyl, tetrahydrofuranonyl, tetrahydrothienyl, tetrahydropyranyl, tetrahydropyranonyl and dioxanyl.

If the group $R^3$ denotes an N-heterocycloalkyl group wherein a methylene group is replaced by CO or $SO_2$, preferred meanings of the group $R^3$ are selected from among pyrrolidinone, piperidinone, piperazinone and morpholinone.

Particularly preferred meanings of $R^3$, particularly if $R^3$ is bound to a C atom, are hydrogen, cyano, hydroxy, $C_{1-6}$-alkyl, $C_{2-6}$-alkynyl, $C_{1-4}$-alkyloxy, $C_{3-10}$-cycloalkyl, $C_{3-10}$-cycloalkyloxy, phenyl, $C_{1-4}$-alkylcarbonyl, $C_{1-4}$-alkyloxycarbonyl, pyrrolidinon-N-yl, pyrazolyl, tetrazolyl and hydroxy, and if $R^3$ is bound to an N atom, $R^3$ particularly preferably denotes hydrogen, cyano, $C_{1-4}$-alkyl, $C_{3-6}$-cycloalkyl, aryl, $C_{1-4}$-alkylcarbonyl or $C_{1-4}$-alkylsulphonyl, while in the cycloalkyl groups one or two methylene units may be replaced independently of one another by O or CO and alkyl groups may be mono- or polyfluorinated, and a phenyl, pyrazolyl or tetrazolyl group may be mono- or disubstituted by identical or different substituents L.

Most particularly preferred groups $R^3$ are hydrogen, cyano, hydroxy, methyl, ethyl, isopropyl, tert.butyl, 2-methylpropyl, phenyl, methoxy, ethoxy, isopropyloxy, cyclopentyloxy, methoxycarbonyl, N-pyrrolidinonyl, 1H-pyrazol-1-yl, 2H-tetrazol-5-yl and 2-methyl-2H-tetrazol-5-yl, and in the event that $R^3$ is bound to an N atom, $R^3$ most particularly preferably denotes hydrogen, methyl, ethyl, isopropyl, tert.butyl, 2-methylpropyl or methylcarbonyl.

If the group $R^3$ is bound to Cy through a double bond, particularly through a C=C double bond, $R^3$ has a meaning selected from the group Y.

The group Y preferably denotes oxygen, $C_{1-6}$-alkyl-methylidene, $C_{2-6}$-alkynyl-methylidene, $C_{2-6}$-alkenyl-methylidene, $C_{3-7}$-cycloalkyl-methylidene or $C_{3-7}$-cycloalkylidene, while the above-mentioned alkyl, alkenyl and alkynyl groups may be partly or completely fluorinated and may be mono- or disubstituted independently of one another by substituents selected from chlorine, hydroxy, $C_{1-3}$-alkoxy and $C_{1-3}$-alkyl, and the above-mentioned unsubstituted methylidene group or the above-mentioned monosubstituted methylidene groups may additionally be monosubstituted by fluorine, $C_{1-3}$-alkyl, trifluoromethyl or cyano, and in a cycloalkylidene group a methylene group may be replaced by O, S or $NR^N$ or an ethylene group may be replaced by $—NR^N—CO—$, $—CO—NR^N—$, $—O—CO—$ or $—CO—O—$.

In the event that in a cycloalkylidene group a methylene group is replaced by O, S or $NR^N$ or an ethylene group is replaced by $—NR^N—CO—$, $—CO—NR^N—$, $—O—CO—$ or $—CO—O—$, the meaning of such a substituted cycloalkylidene group is preferably selected from among dihydrofuranylidene, dihydropyranylidene, dihydrothiophenylidene, pyrrolidinylidene, piperidinylidene, dihydrofuranonylidene, dihydropyranonylidene, pyrrolidinone-ylidene, N-methylpyrrolidinonylidene, piperidinonylidene and N-methylpiperidinonylidene.

Most particularly preferred definitions of the group Y are oxygen, $C_{1-6}$-alkyl-methylidene, $C_{3-7}$-cycloalkyl-methylidene and $C_{3-7}$-cycloalkylidene.

Examples of the most particularly preferred definitions of the group Y are oxygen, ethylidene, isobutylidene, cyclopentyl-methylidene and cyclopentylidene.

According to another preferred variant Y preferably denotes a group according to partial formula T

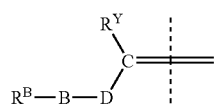

wherein
$R^Y$ denotes hydrogen, fluorine, cyano, trifluoromethyl or $C_{1-3}$-alkyl,
D denotes carbonyl or sulphonyl,
B denotes a single bond, $—O—$ or $—NR^N—$,
$R^B$ denotes $C_{1-6}$-alkyl, $C_{3-7}$-cycloalkyl, $C_{5-7}$-cycloalkenyl, $C_{3-7}$-cycloalkyl-$C_{1-3}$-alkyl, $C_{5-7}$-cycloalkenyl-$C_{1-3}$-alkyl, aryl, heteroaryl, aryl-$C_{1-3}$-alkyl or heteroaryl-$C_{1-3}$-alkyl, while alkyl, cycloalkyl and cycloalkenyl groups may be partly or completely fluorinated or may be mono- or disubstituted by identical or different substituents selected from cyano, hydroxy, $C_{1-3}$-alkoxy and $C_{1-3}$-alkyl, or $R^B$ and B are joined together to form a heterocyclic ring selected from pyrrolidine, morpholine, piperidine, piperazine and 4-($C_{1-4}$-alkyl)-piperazine, while the heterocyclic ring is bound to the group D via the imino group.

If there are cycloalkyl or cycloalkenyl rings in the residues or groups Y, $R^1$ or $R^3$ wherein two methylene groups are replaced by O or S or by CO, SO or $SO_2$, these methylene groups are preferably not joined together directly. If, however, two methylene groups are replaced by O and CO, these may be joined together directly, so as to form a $—O—CO—$ or $—CO—O—$ group. In the event that Y, $R^1$ or $R^3$ is a cycloalkyl or cycloalkenyl group with one or two methylene groups replaced according to the invention, the relevant group Y, $R^1$ or $R^3$ preferably denotes a cycloalkyl or cycloalkenyl group wherein a methylene group is replaced by O, S, CO, SO or $SO_2$ or an ethylene group is replaced by $—O—CO—$ or $—CO—O—$.

Some meanings of other groups and substituents will now be given, which are to be regarded as preferred according to general formula I, formulae I.1 and I.2 and the embodiments described hereinbefore:

Preferred meanings of the group $R^4$ are hydrogen, methyl and fluorine, particularly hydrogen. In the event that $R^4$ is bound to an N atom, $R^4$ preferably denotes hydrogen or methyl.

In the event that $R^3$ and $R^4$ are bound to the same C atom of Cy, $R^3$ and $R^4$ may be joined together such that $R^3$ and $R^4$ together preferably form a $C_{4-5}$-alkylene bridge, wherein one or two methylene units may be replaced independently of one another by O, $NR^N$ or CO. Preferably the groups $R^3$ and $R^4$ joined to one another together with the carbon atom of Cy to which they are attached form a ring selected from cyclopentane, tetrahydrofuran, tetrahydrofuranone, pyrrolidine, pyrrolidinone, dioxolane, dithiolan, cyclohexane, piperidine, piperidinone, tetrahydropyran, tetrahydropyranone, dithian and dioxane, particularly dioxolane.

In the event that $R^3$ and $R^4$ are bound to two adjacent C atoms of the Cy ring, $R^3$ and $R^4$ may be joined together such that $R^3$ and $R^4$ together with the two above-mentioned adjacent atoms of the Cy ring preferably form an anellated cyclohexane, benzene or cyclopentadiene ring, wherein one or two methylene groups may be replaced independently of one another by O, S or $NR^N$ and/or one or two methyne groups may be replaced by N, and which may be mono- or polyfluorinated or mono- or disubstituted by identical or different substituents selected from chlorine, hydroxy, $C_{1-3}$-alkoxy and $C_{1-3}$-alkyl or in the case of an aromatic anellated ring may be mono- or disubstituted by identical or different substituents L.

Preferably the groups $R^3$ and $R^4$ connected to one another form, together with the two above-mentioned adjacent atoms of the Cy ring, an anellated cyclohexane, benzene, furan, thiophene or pyrrole ring, particularly a cyclohexane or benzene ring, which may be mono- or polyfluorinated or mono- or disubstituted by identical or different substituents selected from chlorine, hydroxy, $C_{1-3}$-alkoxy and $C_{1-3}$-alkyl or in the case of an aromatic anellated ring selected from benzene, furan, thiophene or pyrrole may be mono- or disubstituted by identical or different substituents L.

Preferred meanings of the group $R^5$ are hydrogen, methyl and fluorine, particularly hydrogen. In the event that $R^5$ is bound to an N atom, $R^5$ preferably denotes hydrogen or methyl.

In the event that $R^4$ and $R^5$ are joined together and with 2, 3 or 4 atoms of the Cy ring form an anellated or bridged cyclic group, $R^4$ and $R^5$ together preferably represent a $C_{2-4}$-alkylene bridge, wherein one or two methylene units may be replaced independently of one another by O, $NR^N$ or CO. Preferably the groups $R^4$ and $R^5$ attached to one another together with Cy form a bicyclic ring selected from bicyclo[2.2.1]heptane, bicyclo[2.2.2]octane, bicyclo[3.2.1]octane, octahydroindene and decalin, wherein one or two methylene units may be replaced independently of one another by O, $NR^N$ or CO. Particularly preferably the attached groups $R^4$ and $R^5$ together with Cy form a bicyclo[3.2.1]octane system.

If in the above-mentioned bicyclic rings one or two methylene units are replaced independently of one another by O, $NR^N$ or CO, preferred meanings include decahydroquinoline, decahydroisoquinoline, octahydroquinolinone, octahydroisoquinolinone, decahydroquinoxaline, octahydroquinoxalinone, octahydrobenzoxazine.

Preferred meanings of the group $R^6$ are hydrogen, methyl and fluorine, particularly hydrogen. In the event that $R^6$ is bound to an N atom, $R^6$ preferably denotes hydrogen or methyl.

In the event that the groups $R^4$, $R^5$ and $R^6$ are joined together, together they preferably form a $C_{4-5}$-alkanetriyl bridge which together with the Cy ring forms a tricyclic system, while the alkanetriyl bridge may be mono- or polyfluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, CO, $SO_2$ or $NR^N$. Preferably the $C_{4-5}$-alkanetriyl bridge together with the Cy ring forms a tricyclic system selected from tricyclononane, tricyclodecane and tricycloundecane, particularly preferably adamantane, which may be unsubstituted or mono- or polyfluorinated or mono- or disubstituted by identical or different substituents selected from chlorine, hydroxy, $C_{1-3}$-alkoxy and $C_{1-3}$-alkyl.

Preferred meanings of the group Z are —O—, —$CH_2$—, —$CF_2$—, —$C(CH_3)_2$—, —CH═, —$NR^N$—, and —CO—, particularly —O—, —$CH_2$— and —CH═, most particularly preferably —$CH_2$— and —O—.

The substituents $R^{7a}$, $R^{7b}$, $R^{7c}$, $R^{7d}$ independently of one another preferably represent hydrogen, ($C_{1-8}$-alkyl)oxycarbonyl, ($C_{1-18}$-alkyl)carbonyl, benzoyl, particularly hydrogen or ($C_{1-6}$-alkyl)oxycarbonyl, ($C_{1-8}$-alkyl)carbonyl, particularly preferably hydrogen, methoxycarbonyl, ethoxycarbonyl, methylcarbonyl or ethylcarbonyl. Most particularly preferably $R^{7a}$, $R^{7b}$, $R^{7c}$ and $R^{7d}$ represent hydrogen.

The compounds of formula I wherein $R^{7a}$, $R^{7b}$, $R^{7c}$ and $R^{7d}$ have a meaning according to the invention which is other than hydrogen, for example $C_{1-8}$alkylcarbonyl, are preferably suitable as intermediate products in the synthesis of compounds of formula I wherein $R^{7a}$, $R^{7b}$, $R^{7c}$ and $R^{7d}$ represent hydrogen.

The substituents L are preferably selected independently of one another from among fluorine, chlorine, bromine, $C_{1-3}$-alkyl, difluoromethyl, trifluoromethyl, $C_{1-3}$-alkoxy, difluoromethoxy, trifluoromethoxy and cyano, particularly preferably from among fluorine, chlorine, methyl, trifluoromethyl, methoxy and difluoromethoxy. If the substituent L is linked to an N atom, preferred meanings L are selected from $C_{1-3}$-alkyl, difluoromethyl and trifluoromethyl.

Particularly preferred compounds of general formula I are selected from among formulae I.1a to I.1d and I.2a to I.2d, particularly formula I.1c and I.2c:

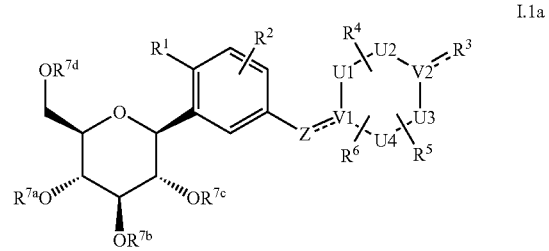

I.1a

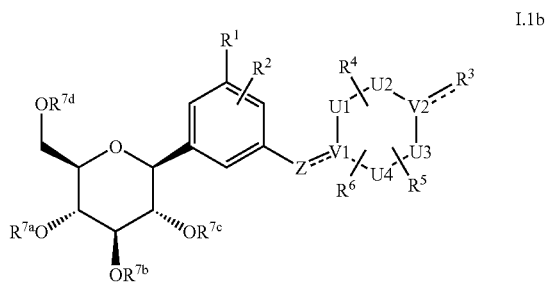

I.1b

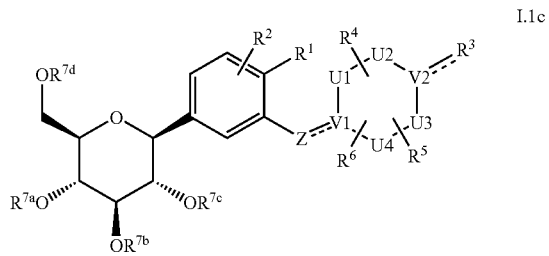

I.1c

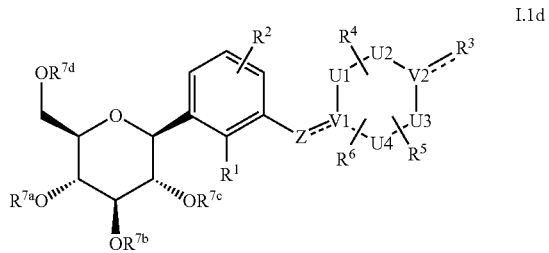

I.1d

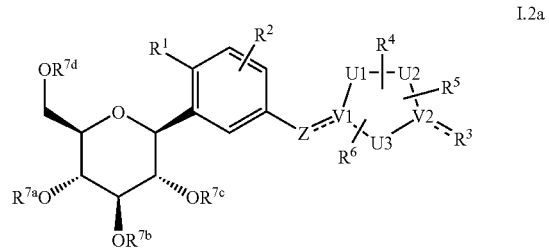

I.2a

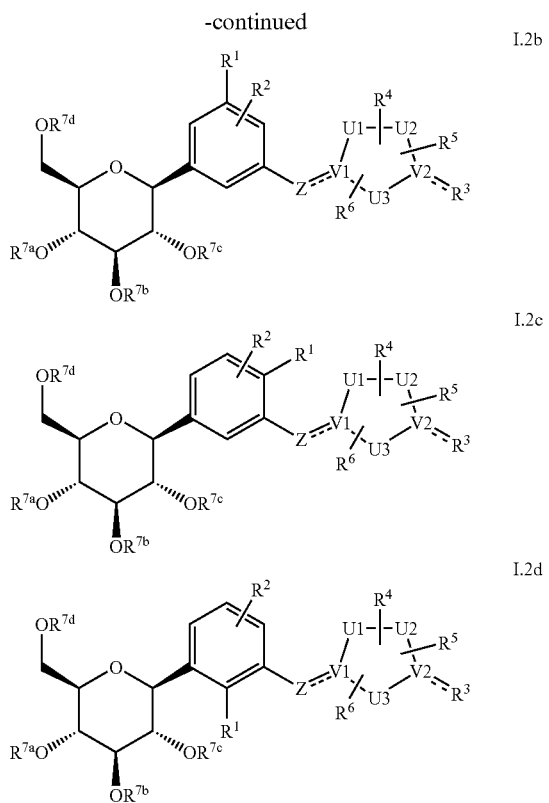

wherein
V1, V2 independently of one another represent C or N,
U1, U2,
U3, U4 independently of one another represent C, N, O, CO or $SO_2$, with the proviso that in the ring formed by U and V there are a maximum of 2 heteroatoms selected from N and O, which are not directly joined together, and there is a maximum of one group selected from CO and $SO_2$, and remaining free chemical bonds to C and N atoms are saturated with hydrogen; and wherein $R^1$ to $R^6$, Z, $R^{7a}$, $R^{7b}$, $R^{7c}$, $R^{7d}$ are as hereinbefore defined.

Most particularly preferred are those compounds of formulae I.1a, I.1b, I.1c and I.1d, particularly of formula I.1c, wherein the groups U1, U2, U3, U4, V1 and V2 represent carbon, i.e. the cyclic group formed by the groups U and V denotes cyclohexane.

Most particularly preferred are those compounds of formulae I.1a to I.1d or 1.2a to 1.2d, particularly of formula I.1c and 1.2c, wherein the groups $R^1$ to $R^6$, Z, $R^{7a}$, $R^{7b}$, $R^{7c}$, $R^{7d}$ have the meanings given hereinbefore as being preferred, particularly wherein $R^1$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or completely fluorinated; particularly preferably denotes hydrogen, fluorine, chlorine, bromine, methyl, ethyl, isopropyl, trifluoromethyl, ethynyl, methoxy, cyclopentyloxy or cyano; and $R^3$ (1) denotes hydrogen, cyano, hydroxy, $C_{1-6}$-alkyl, $C_{2-6}$-alkynyl, $C_{1-4}$-alkyloxy, $C_{3-7}$-cycloalkyl, $C_{3-7}$-cycloalkyloxy, phenyl, $C_{1-4}$-alkylcarbonyl, $C_{1-4}$-alkyloxycarbonyl, pyrrolidinon-N-yl, pyrazolyl, tetrazolyl or hydroxy, and in the event that $R^3$ is bound to an N atom, $R^3$ preferably denotes hydrogen, cyano, $C_{1-4}$-alkyl, $C_{3-6}$-cycloalkyl, aryl, $C_{1-4}$-alkylcarbonyl or $C_{1-4}$-alkylsulphonyl, while in the cycloalkyl groups one or two methylene units may be replaced independently of one another by O or CO and alkyl groups may be partly or completely fluorinated, and the phenyl group may be mono- or disubstituted by identical or different substituents L; particularly preferably $R^3$ denotes hydrogen, cyano, hydroxy, methyl, ethyl, isopropyl, tert.butyl, 2-methylpropyl, phenyl, methoxy, ethoxy, isopropyloxy, cyclopentyloxy, methoxycarbonyl, N-pyrrolidinonyl, 1H-pyrazol-1-yl, 2H-tetrazol-5-yl or 2-methyl-2H-tetrazol-5-yl, and in the event that $R^3$ is bound to an N atom, $R^3$ particularly preferably denotes hydrogen, methyl, ethyl, isopropyl, tert.butyl, 2-methylpropyl or methylcarbonyl; or (2) denotes

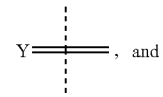, and and

Y (1) denotes oxygen; or
(2) denotes $C_{1-6}$-alkyl-methylidene, $C_{2-6}$-alkynyl-methylidene, $C_{2-6}$-alkenyl-methylidene, $C_{3-7}$-cycloalkyl-methylidene or $C_{3-7}$-cycloalkylidene, while the above-mentioned alkyl, alkenyl and alkynyl groups may be partly or completely fluorinated and may be mono- or disubstituted independently of one another by substituents selected from chlorine, hydroxy, $C_{1-3}$-alkoxy and $C_{1-3}$-alkyl, the above-mentioned unsubstituted methylidene group or the above-mentioned monosubstituted methylidene groups may additionally be monosubstituted by fluorine, $C_{1-3}$-alkyl, trifluoromethyl or cyano, and in a cycloalkylidene group a methylene group may be replaced by O, S or $NR^N$ or an ethylene group may be replaced by —$NR^N$—CO—, —CO—$NR^N$—, —O—CO— or —CO—O—;

particularly preferably X denotes $C_{1-6}$-alkyl-methylidene, $C_{3-6}$-cycloalkyl-methylidene or $C_{3-7}$-cycloalkylidene; or (3) denotes a group according to partial formula T

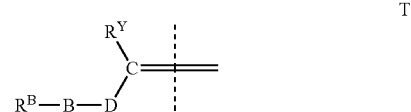

wherein
$R^Y$ denotes hydrogen, fluorine, cyano, trifluoromethyl or $C_{1-3}$-alkyl,
D denotes carbonyl or sulphonyl,
B denotes a single bond, —O or —$NR^N$—, $R^B$ denotes $C_{1-6}$-alkyl, $C_{3-7}$-cycloalkyl, $C_{5-7}$-cycloalkenyl, $C_{3-7}$-cycloalkyl-$C_{1-3}$-alkyl, $C_{5-7}$-cycloalkenyl-$C_{1-3}$-alkyl, aryl, heteroaryl, aryl-$C_{1-3}$-alkyl or heteroaryl-$C_{1-3}$-alkyl, while alkyl, cycloalkyl and cycloalkenyl groups may be partly or completely fluorinated or may be mono- or disubstituted by identical or different substituents selected from cyano, hydroxy, $C_{1-3}$-alkoxy and $C_{1-3}$-alkyl, or $R^B$ and B are joined together to form a heterocyclic ring selected from pyrrolidine, morpholine, piperidine, piperazine and 4-($C_{1-4}$-alkyl)-piperazine, while the heterocyclic ring is bound to the C=O group via the imino group;

$R^2$ denotes hydrogen, fluorine, chlorine, bromine, methyl, hydroxy, methoxy, ethoxy, trifluoromethoxy, cyano, nitro or methyl substituted by 1 to 3 fluorine atoms, particularly preferably hydrogen, fluorine, hydroxy, methoxy, ethoxy or methyl, particularly hydrogen or methyl, and $R^4$, $R^5$, $R^6$ in each case independently of one another denote hydrogen, methyl or fluorine, particularly hydrogen, and in the event that the substituent is bound to an N atom, in each case independently denotes hydrogen or methyl; or the groups $R^4$, $R^5$ and $R^6$ are joined together, forming a $C_{4-5}$-alkanetriyl bridge, and together with the Cy ring form a tricyclic system selected from tricyclononane, tricyclodecane and tricycloundecane, particularly preferably adamantane, which is unsubstituted or may be mono- or polyfluorinated or mono- or disubstituted by identical or different substituents selected from chlorine, hydroxy, $C_{1-3}$-alkoxy and $C_{1-3}$-alkyl;

Z denotes oxygen, methylidene or methylene, particularly preferably methylene, and $R^{7a}$, $R^{7b}$, $R^{7c}$, $R^{7d}$ independently of one another represent hydrogen, ($C_{1-8}$-alkyl)oxycarbonyl, ($C_{1-18}$-alkyl)carbonyl or benzoyl, particularly hydrogen or ($C_{1-6}$-alkyl)oxycarbonyl, ($C_{1-8}$-alkyl)carbonyl, particularly preferably hydrogen, methoxycarbonyl, ethoxycarbonyl, methylcarbonyl or ethylcarbonyl, most particularly preferably hydrogen, and L independently of one another represent fluorine, chlorine, bromine, $C_{1-3}$-alkyl, difluoromethyl, trifluoromethyl, $C_{1-3}$-alkoxy, difluoromethoxy, trifluoromethoxy or cyano; and if L is bound to an N atom, independently of one another represent $C_{1-3}$-alkyl, difluoromethyl or trifluoromethyl;

including the tautomers, the stereoisomers, the mixtures thereof and the salts thereof, particularly the physiologically acceptable salts thereof.

According to a variant of the foregoing embodiments, compounds wherein the cyclic group Cy which carries the substituent $R^3$ has at least one other substituent $R^4$, $R^5$ and/or $R^6$ other than hydrogen are also preferred. According to this variant compounds which have a substituent $R^4$ representing methyl or fluorine are also preferred.

Particularly preferred compounds of general formula I are selected from among:
(a) 1-chloro-2-(4-methoxy-cyclohexyloxy)-4-(β-D-glucopyranos-1-yl)-benzene,
(b) 1-chloro-2-(cyclohexylmethyl)-4-(β-D-glucopyranos-1-yl)-benzene,
(c) 1-chloro-2-(4-methoxy-cyclohexylmethyl)-4-(β-D-glucopyranos-1-yl)-benzene,
(d) 1-chloro-2-(cis-4-methoxy-cyclohexyloxy)-4-(β-D-glucopyranos-1-yl)-benzene
(e) 1-chloro-2-(trans-4-methoxy-cyclohexyloxy)-4-(β-D-glucopyranos-1-yl)-benzene
(f) 1-chloro-2-(4,4-dimethyl-cyclohexyloxy)-4-(β-D-glucopyranos-1-yl)-benzene,
(g) 1-chloro-2-(1,2,3,4-tetrahydronaphth-2-yloxy)-4-(β-D-glucopyranos-1-yl)-benzene,
(h) 1-chloro-2-(tetrahydropyran-4-yloxy)-4-(β-D-glucopyranos-1-yl)-benzene,
(i) 1-chloro-2-(cis-3-methoxy-cyclopent-1-yloxy)-4-(β-D-glucopyranos-1-yl)-benzene,
(j) 1-chloro-2-(tetrahydropyran-4-ylmethyl)-4-(β-D-glucopyranos-1-yl)-benzene,
(k) 1-chloro-2-(4,4-dimethyl-cyclohexylmethyl)-4-(β-D-glucopyranos-1-yl)-benzene,
(l) 1-chloro-2-(4-methoxy-cyclohexylmethyl)-4-(β-D-glucopyranos-1-yl)-benzene,
(m) 1-chloro-2-(adamant-2-ylmethyl)-4-(β-D-glucopyranos-1-yl)-benzene, including the tautomers, the stereoisomers and the mixtures thereof.

Some terms used above and hereinafter to describe the compounds according to the invention will now be defined more closely.

The term halogen denotes an atom selected from the group consisting of F, Cl, Br and I, particularly F, Cl and Br.

The phrases "may be partly or completely fluorinated" and "may be mono- or polyfluorinated" which are used interchangeably indicate that the group thus designated is not fluorinated or comprises one or more fluorine substituents, and this also includes total fluorination of the group indicated.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term methylene denotes a —$CH_2$ group and the term methyne denotes a CH group.

The term methylidene denotes a group of the partial formula

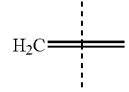

attached by a double bond.

The term $C_{1-n}$-alkyl-methylidene denotes a methylidene group wherein a hydrogen atom is substituted by a $C_{1-n}$-alkyl group.

The term methanylylidene denotes a CH bridge of the partial formula

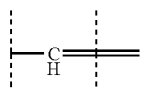

attached via a single bond and a double bond.

The term "butadienylene" denotes the group

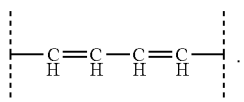

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl etc. Unless stated otherwise, alkynyl groups are linked to the rest of the molecule via the C atom in position 1. Therefore, terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, decalin, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{3-n}$-cycloalkyloxy denotes a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{5-n}$-cycloalkenyl denotes a $C_{5-n}$-cycloalkyl group which is as hereinbefore defined and additionally comprises at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-4}$-alkyl)silyl comprises silyl groups which comprise identical alkyl groups or two or three different alkyl groups.

The term di-($C_{1-3}$-alkyl)amino comprises amino groups which have identical alkyl groups or two different alkyl groups.

The term N-heterocycloalkyl denotes a saturated carbocyclic ring which comprises an imino group in the ring, and which may additionally comprise another optionally substituted imino group or an O or S atom in the ring. By an imino group is meant the group —NH—. Examples of such N-heterocycloalkyl groups are pyrrolidine, piperidine, piperazine, N-alkyl-piperazine and morpholine.

If alkyl radicals occurring in groups, for example in X, $R^1$ or $R^3$, may be substituted, e.g. fluorinated, this encompasses not only alkyl radicals in the groups which represent alkyl directly but also in other definitions which include alkyl groups, such as for example alkoxy, alkylcarbonyl, alkoxyalkyl, etc. Thus, for example X, $R^1$ and $R^3$ representing alkoxy, wherein the alkyl groups may be partly or totally fluorinated, also include difluoromethoxy and trifluoromethoxy.

The style used above and hereinafter, in which a bond of a substituent in a cyclic group, for example a phenyl group or in the group Cy, is shown towards the centre of the phenyl ring, denotes, unless otherwise stated, that this substituent may be bound to any free position of the cyclic group bearing an H atom. Thus, two substituents may also be bound to a methylene group of the cyclic group.

The compounds according to the invention may be obtained using methods of synthesis known in principle. Preferably the compounds are obtained by the following methods according to the invention which are described in more detail hereinafter.

The glucose derivatives described hereinafter may be synthesised from D-gluconolactone or a derivative thereof by addition of the desired aryl group in the form of an organometallic compound (Diagram 1).

Diagram 1: Addition of an organometallic compound to a gluconolactone

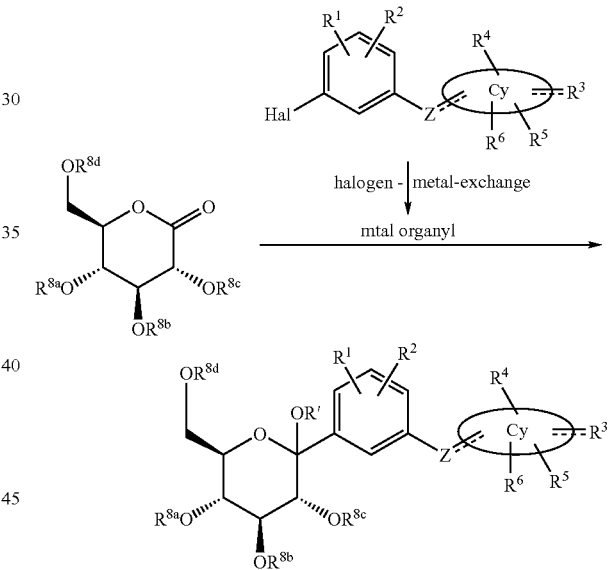

The reaction according to Diagram 1 is best carried out starting from aromatic groups substituted with chlorine, bromine or iodine. The corresponding organometallic compound may be prepared therefrom either by a so-called halogen-metal exchange or by inserting the metal into the carbon-halogen bond. The halogen-metal exchange may be carried out for example with an organolithium compound such as e.g. n-, sec. or tert.butyllithium and thereby yields the corresponding lithiated aromatic group. The analogous magnesium compound may also be generated by a halogen-metal exchange with a suitable Grignard compound such as e.g. isopropylmagnesium bromide or diisopropylmagnesium. The reactions are preferably carried out between 0 and −100° C., particularly preferably between −30 and −80° C. in solvents such as for example ether, tetrahydrofuran, toluene, hexane or methylene chloride. The magnesium or lithium compounds thus obtained may be transmetallated with metal salts such as e.g. cerium trichloride, to produce other organometal compounds suitable for the addition. Alternatively the organometallic compounds may also be prepared by inserting a metal in the carbon-halogen bond of an aryl chloride, bromide or iodide. Suitable metals for this purpose are e.g. lithium or magnesium. The addition of the organometallic compounds to the gluconolactone or derivatives thereof is preferably carried out at temperatures between 0 and −100° C., particularly preferably at −30 to −80° C. Suitable solvents include e.g. ethers, toluene, methylene chloride, hexane, tetrahydrofuran or mixtures thereof (see M. Schlosser, Organometallics in Synthesis, John Wiley & Sons, Chichester/New York/Brisbane/Toronto/Singapore, 1994).

The methods of synthesising the aromatic groups are standard transformations in organic chemistry and are part of the general knowledge in the art or are at least known from the specialist literature as methods in organic synthesis and would readily be available to the skilled man with respect to the compounds according to the invention (see inter alia J. March, Advanced Organic Reactions, Reactions, Mechanisms, and Structure, 4th Edition, John Wiley & Sons, Chichester/New York/Brisbane/Toronto/Singapore, 1992 and literature cited therein and synthesis examples I-IX, XI-XIV and 2).

In order to prepare compounds of general formula I according to process a) of the invention, a compound of general formula II

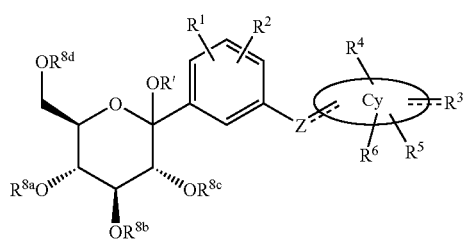

wherein Z, Cy and R', $R^1$ to $R^6$ are as hereinbefore defined and $R^{8a}$, $R^{8b}$, $R^{8c}$ and $R^{8d}$ are as hereinbefore defined and independently of one another represent for example acetyl, pivaloyl, benzoyl, tert.-butoxycarbonyl, benzyloxycarbonyl, trialkylsilyl, benzyl or substituted benzyl, is reacted with a reducing agent in the presence of an acid.

Suitable reducing agents for the reaction include for example silanes, such as triethyl-, tripropyl-, triisopropyl- or diphenylsilane, sodium borohydride, sodium cyanoborohydride, zinc borohydride, borane, lithium aluminium hydride, diisobutylaluminium hydride or samarium iodide. The reductions are preferably carried out in the presence of a suitable acid, such as e.g. hydrochloric acid, toluenesulphonic acid, trifluoroacetic acid, acetic acid, boron trifluoride etherate, trimethylsilyltriflate, titanium tetrachloride, tin tetrachloride, scandium triflate or zinc iodide. Depending on the reducing agent and the acid the reaction may be carried out in a solvent, such as for example methylene chloride, chloroform, acetonitrile, toluene, hexane, diethyl ether, tetrahydrofuran, dioxane, ethanol, water or mixtures thereof at temperatures between −60° C. and 120° C. A particularly suitable combination of reagents consists for example of triethylsilane and boron trifluoride etherate, which is conveniently used in acetonitrile or dichloromethane at temperatures of −60° C. and 60° C. Moreover, hydrogen may be used in the presence of a transition metal catalyst such as e.g. palladium on charcoal or Raney nickel, in solvents such as tetrahydrofuran, ethyl acetate, methanol, ethanol, water or acetic acid, for the transformation described.

Alternatively, in order to prepare compounds of general formula I according to method b) of the invention, in a compound of general formula III

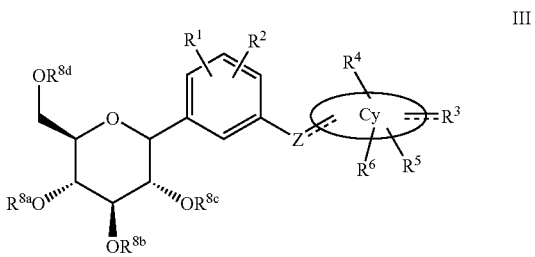

wherein Cy, Z and $R^1$ to $R^6$ are as hereinbefore defined and $R^{8a}$ to $R^{8d}$ denotes one of the protective groups defined hereinbefore, such as e.g. an acyl, arylmethyl, acetal, ketal or silyl group, the protective groups are cleaved.

Any acyl, acetal or ketal protecting group used is cleaved, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C. A trifluoroacetyl group is preferably cleaved by treatment with an acid such as hydrochloric acid, optionally in the presence of a solvent such as acetic acid, at temperatures between 50 and 120° C. or by treatment with sodium hydroxide solution, optionally in the presence of a solvent such as tetrahydrofuran or methanol, at temperatures between 0 and 50° C.

A trimethylsilyl group is cleaved for example in water, an aqueous solvent mixture or a lower alcohol such as methanol or ethanol in the presence of a base such as lithium hydroxide, sodium hydroxide, potassium carbonate or sodium methoxide. In aqueous or alcoholic solvents, acids such as e.g. hydrochloric acid, trifluoroacetic acid or acetic acid are also suitable. Fluoride reagents, such as e.g. tetrabutylammonium fluoride, are also suitable for cleaving in organic solvents, such as for example diethyl ether, tetrahydrofuran or dichloromethane.

A benzyl, methoxybenzyl or benzyloxycarbonyl group is advantageously cleaved hydrogenolytically, e.g. with hydrogen in the presence of a catalyst such as palladium/charcoal, in a suitable solvent such as methanol, ethanol, ethyl acetate or glacial acetic acid, optionally with the addition of an acid such as hydrochloric acid, at temperatures between 0 and 100° C., but preferably at ambient temperature between 20 and 60° C., and under a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert.-butyloxycarbonyl group is preferably cleaved by treatment with an acid such as trifluoroacetic acid or hydrochloric acid or by treatment with iodotrimethylsilane, optionally using a solvent such as methylene chloride, dioxane, methanol or diethyl ether.

In the reactions described hereinbefore, any reactive groups present such as ethynyl, hydroxy, amino, alkylamino or imino groups may be protected during the reaction by conventional protecting groups which are cleaved again after the reaction, e.g. as described above.

For example, a protecting group for an ethynyl group may be a trimethylsilyl group.

For example, a protecting group for a hydroxy group may be a trimethylsilyl, acetyl, trityl, benzyl or tetrahydropyranyl group.

Examples of protecting groups for an amino, alkylamino or imino group include the formyl, acetyl, trifluoroacetyl, ethoxycarbonyl, tert.-butoxycarbonyl, benzyloxycarbonyl, benzyl, methoxybenzyl or 2,4-dimethoxybenzyl group.

Furthermore, the compounds of general formula I thus obtained may be selectively derivatised at a hydroxy group or the hydroxy group itself may be substituted.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds of general formulae II and III used as starting materials are partly known from the literature or may be obtained by methods known from the literature and also analogously to the methods described in the Examples, optionally with the additional inclusion of protecting groups.

The compounds according to the invention may advantageously also be obtained by the methods described in the following Examples, which may also be combined with methods known to the skilled man from the literature, for example, particularly the methods described in WO 98/31697, WO 01/27128, WO 02/083066, WO 03/099836, WO 04/063209 and WO 04/76470.

As already mentioned hereinbefore, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}$C-labelled alpha-methyl-glucopyranoside ($^{14}$C-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen).

The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% $CO_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

Alternatively, measurement of the cellular membrane potential for hSGLT1 and hSGLT2 may also be used for the biological testing of substances. The cell models described earlier may be used for this. For the test, 10,000 cells per well of a black 384-well plate with a transparent base coated with poly-D-lysine are seeded in culture medium and incubated for 16 hours at 37° C., 5% $CO_2$. Then the cells are washed twice with glucose-free HBSS buffer (12.67 mol/l $CaCl_2$, 4.93 mmol/l $MgCl_2$, 4.07 mmol/l $MgSO_4$, 4.41 mmol/l $KH_2PO_4$; pH 7.4) and covered with 20 µl HBSS. After the addition of 20 µl, of charging buffer (Membrane Potential Assay Kit Explorer R8126, Molecular Devices GmbH, Ismaning) and 20 µl, of the substance to be tested in a suitable concentration, incubation is continued for a further 30 min. at 37° C., 5% $CO_2$. The measurement is carried out in the Fluorescent Imaging Plate Reader (Molecular Devices GmbH, Ismaning) at an excitation wavelength of 485 nm and is started by the addition of 20 µl of stimulant buffer (140 mM NaCl and 120 mM glucose). The depolarisation of the cell caused by the glucose-induced influx of $Na^+$ can be measured and quantified as a change in fluorescence.

The compounds of general formula I according to the invention may for example have EC50 values of less than 1000 nM, particularly less than 200 nM, particularly preferably less than 50 nM.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, solutions, suspensions or suppositories.

The compounds according to the invention may also be used in conjunction with other active substances, particularly for the treatment and/or prevention of the diseases and conditions mentioned above. Other active substances which are suitable for such combinations include, in particular, those which potentiate the therapeutic effect of an SGLT inhibitor according to the invention with respect to one of the indications mentioned and/or which allow the dosage of an SGLT inhibitor according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK431), alpha2-antagonists, insulin and insulin analogues, GLP-1 and GLP-1 analogues (e.g. exendin-4) or amylin. Other active substances which are suitable as combination partners include inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-increasing compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramate, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

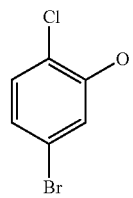

5-bromo-2-chloro-phenol 96 ml of a 1 M solution of boron tribromide in dichloromethane are added to an ice-cooled solution of 20 g 5-bromo-2-chloro-anisol in 300 ml dichloromethane. The reaction solution is stirred for 14 h at ambient temperature and then cooled in the ice bath. The cooled solution is combined with aqueous saturated potassium carbonate solution, the aqueous phase is acidified with 1 M hydrochloric acid and extracted with dichloromethane. The combined organic phases are dried over sodium sulphate and the solvent is eliminated completely.

Yield: 17.9 g (96% of theory)

Mass spectrum (ESI$^+$): m/z=205/207/209 (bromine+chlorine) [M+H]$^+$

EXAMPLE II

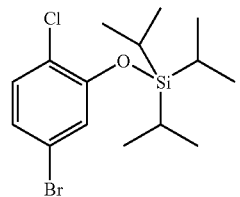

1-bromo-4-chloro-3-(tri-isopropyl-silyloxy)-benzene 9.2 g triisopropylsilyl chloride in 20 ml dichloromethane and then 0.5 g 4-dimethylaminopyridine are added to an ice-cooled solution of 9.2 g 5-bromo-2-chloro-phenol and 9.4 ml triethylamine in 120 ml dichloromethane. The reaction is stirred for 18 h at ambient temperature and then diluted with 100 ml dichloromethane. The diluted solution is washed with 1 M hydrochloric acid and aqueous sodium hydrogen carbonate solution, dried over sodium sulphate and the solvent is removed. The residue is purified on silica gel (cyclohexane/ethyl acetate 9:1->1:1).

Yield: 9.4 g (59% of theory)

Mass spectrum (ESI$^+$): m/z=363/365/367 (bromine+chlorine) [M+H]$^+$

EXAMPLE III

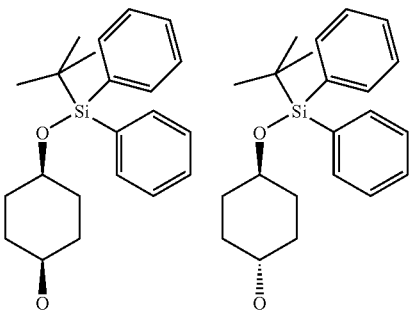

cis-4-(tert-butyl-diphenylsilyloxy)-cyclohexanol and
trans-4-(tert-butyl-diphenylsilyloxy)-cyclohexanol A solution of 29.4 g tert-butyldiphenylsilyl chloride in 20 ml of dimethylformamide is added dropwise to an ice-cooled solution of 10.0 g 1,4-cyclohexanediol (cis/trans mixture approx. 1:1) and 14.6 g imidazole in 15 ml dry dimethylformamide and 20 ml dry tetrahydrofuran. The reaction solution is stirred for 1 h in the ice bath and then combined with 100 ml aqueous sodium chloride solution. The organic phase is separated off and the aqueous phase is extracted with ethyl acetate. The combined organic phases are dried over sodium sulphate, and the solvent is eliminated totally. The residue is purified by chromatography and resolved into the two isomeric products (ethyl acetate/cyclohexane 1:1).

cis-4-(tert-butyl-diphenylsilyloxy)-cyclohexanol:
Yield: 4.9 g (16% of theory)
Mass spectrum (ESI$^+$): m/z=355 [M+H]$^+$
trans-4-(tert-butyl-diphenylsilyloxy)-cyclohexanol:
Yield: 4.8 g (16% of theory)
Mass spectrum (ESI$^+$): m/z=355 [M+H]$^+$

EXAMPLE IV

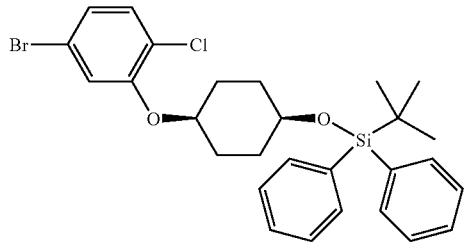

1-bromo-3-[cis-4-(tert-butyl-diphenylsilyloxy)-cyclohexyloxy]-4-chloro-benzene 4.8 g of 5-bromo-2-chloro-phenol, 4.5 g triphenylphosphine and 3.3 ml diisopropyl azodicarboxylate are added to a solution of 1.85 g trans-4-(tert-butyl-diphenylsilyloxy)-cyclohexanol in 20 ml dry tetrahydrofuran in the order stated. The solution is stirred for 48 h at 55° C. and then combined with aqueous potassium carbonate solution. Then the mixture is extracted with ethyl acetate, dried over sodium sulphate and the solvent is removed. The residue is purified on silica gel (cyclohexane/ethyl acetate 4:1).

Yield: 3.5 g (72% of theory)
Mass spectrum (ESI$^+$): m/z=543/545/547 (bromine and chlorine) [M+H]$^+$ The following compounds are obtained analogously to Example IV:

(1) 1-bromo-3-[trans-4-(tert-butyl-diphenylsilyloxy)-cyclohexyloxy]-4-chloro-benzene

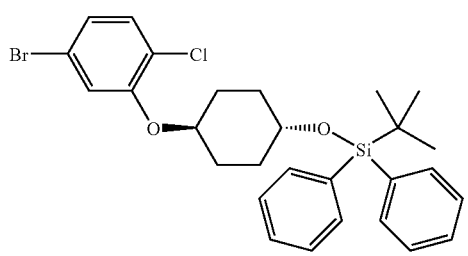

Mass spectrum (ESI$^+$): m/z=543/545/547 (bromine and chlorine) [M+H]$^+$ (2) 1-bromo-3-(4.4-dimethylcyclohexyloxy)-4-chloro-benzene

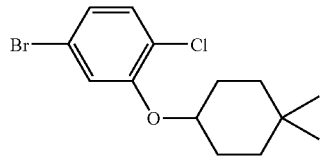

(3) 1-bromo-3-(1,2,3,4-tetrahydronaphth-2-yloxy)-4-chloro-benzene

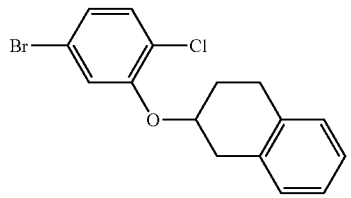

(4) 1-bromo-3-(tetrahydropyran-4-yloxy)-4-chloro-benzene

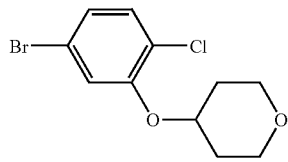

Mass spectrum (ESI$^+$): m/z=291/293/295 (bromine and chlorine) [M+H]$^+$

EXAMPLE V

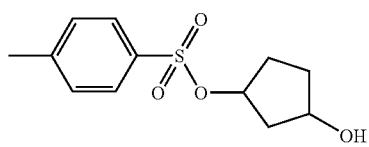

3-(4-methyl-phenylsulphonyloxy)-cyclopentanol

A solution of 9.00 g p-toluenesulphonic acid chloride in 30 ml dichloromethane is added dropwise to an ice-cooled solution of 4.97 g cyclopentan-1,3-diol (cis/trans mixture) in 15 ml of pyridine and 10 ml dichloromethane. The solution is stirred for 45 min at 15° C. The solution is diluted with 100 ml dichloromethane, washed twice with 2 N hydrochloric acid and once with water. After drying through sodium sulphate and elimination of the solvent the product is obtained as a brown oil.

Yield: 6.83 g (58% of theory)
Mass spectrum (ESI$^+$): m/z=274 [M+NH$_4$]$^+$

EXAMPLE VI

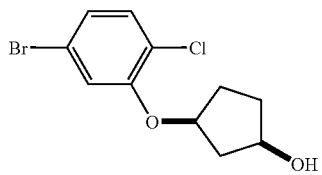

1-bromo-3-(cis-3-hydroxy-cyclopent-1-yloxy)-4-chloro-benzene 12.11 g caesium carbonate are added to a solution of 5.50 g 5-bromo-2-chloro-phenol in 100 ml of dimethylformamide. The suspension is stirred for 15 min at ambient temperature and then 6.83 g 3-(4-methyl-phenylsulphonyloxy)-cyclopentanol (cis/trans mixture) are added. The mixture is stirred for 16 h at 65° C. and then combined with aqueous sodium chloride solution. The mixture is extracted with ethyl acetate, the organic extracts are dried over sodium sulphate, and the solvent is removed. The residue is purified on silica gel (cyclohexane/ethyl acetate 9:1->2:1).

Yield: 3.90 g (50% of theory)

Mass spectrum (ESI$^+$): m/z=290/292/294 (bromine and chlorine) [M]$^+$

EXAMPLE VII

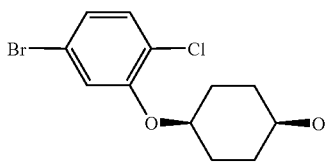

1-bromo-4-chloro-3-(cis-4-hydroxy-cyclohexyloxy)-benzene 8.8 ml of a 1 M solution of tetrabutylammonium fluoride in tetrahydrofuran are added to an ice-cooled solution of 4.8 g 1-bromo-3-[cis-4-(tert-butyl-diphenylsilyloxy)-cyclohexyloxy]-4-chloro-benzene in 25 ml dry tetrahydrofuran. The solution is stirred for 14 h at ambient temperature and then combined with water. Then the mixture is extracted with ethyl acetate, dried over sodium sulphate and the solvent is removed. The residue is purified on silica gel (cyclohexane/ethyl acetate 1:0->3:2).

Yield: 2.1 g (79% of theory)

Mass spectrum (ESI$^+$): m/z=327/329/331 (bromine and chlorine) [M+Na]$^+$

The following compound is obtained analogously to Example VII:

(1) 1-bromo-4-chloro-3-(trans-4-hydroxy-cyclohexyloxy)-benzene

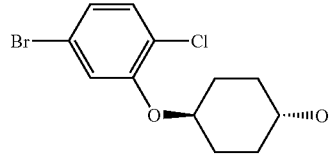

Mass spectrum (ESI$^+$): m/z=327/329/331 (bromine and chlorine) [M+Na]$^+$

EXAMPLE VIII

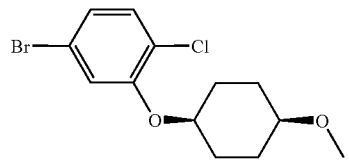

1-bromo-4-chloro-3-(cis-4-methoxy-cyclohexyloxy)-benzene

Under an argon atmosphere 0.28 g sodium hydride (60% in mineral oil) are added to an ice-cooled solution of 2.1 g 1-bromo-4-chloro-3-(cis-4-hydroxy-cyclohexyloxy)-benzene in 10 ml dry tetrahydrofuran. The solution is stirred for 30 min in the ice bath and then 0.44 ml methyl iodide are added. The reaction solution is stirred for 6 h at ambient temperature and then combined with water. Then the mixture is extracted with ethyl acetate, dried over sodium sulphate and the solvent is removed. The residue is purified on silica gel (cyclohexane/ethyl acetate 1:0->1:1).

Yield: 1.8 g (80% of theory)

Mass spectrum (ESI$^+$): m/z=319/321/323 (bromine and chlorine) [M+H]$^+$

The following compounds are obtained analogously to Example VIII:

(1) 1-bromo-4-chloro-3-(trans-4-methoxy-cyclohex-1-yloxy)-benzene

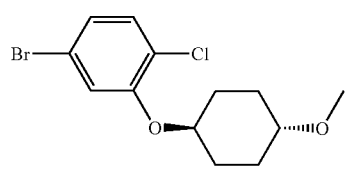

Mass spectrum (ESI$^+$): m/z=319/321/323 (bromine and chlorine) [M+H]$^+$

(2) 1-bromo-4-chloro-3-(cis-3-methoxy-cyclopent-1-yloxy)-benzene

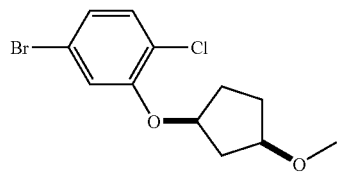

Mass spectrum (ESI$^+$): m/z=305/307/309 (bromine and chlorine) [M+H]$^+$

EXAMPLE IX

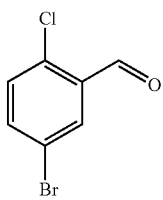

5-bromo-2-chloro-benzaldehyde 7 ml dimethylsulphoxide in 25 ml dichloromethane are added dropwise to a solution of 4.4 ml oxalyl chloride in 125 ml dichloromethane cooled to −60° C. After 5 min stirring a solution of 10.0 g 5-bromo-2-chloro-benzylalcohol in 50 ml of tetrahydrofuran is added and the mixture is stirred for a further 15 min at −60° C. Then 31.5 ml triethylamine are added and the reaction solution is allowed to come up to ambient temperature in the cooling bath. At ambient temperature water is added, the organic phase is separated off and washed with 1 M hydrochloric acid. After drying through sodium sulphate the solvent is eliminated totally.

Yield: 9.7 g (98% of theory)

Mass spectrum (ESI$^+$): m/z=218/220/222 (bromine+chlorine) [M+H]$^+$

EXAMPLE X

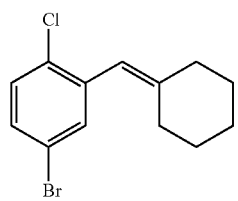

1-bromo-4-chloro-3-cyclohexylidenemethyl-benzene 3.55 ml of a 1.9 M solution phenyllithium in diethyl ether/cyclohexane (70/30) are added dropwise to an ice-cooled solution of 2.9 g cyclohexyl-triphenylphosphonium bromide in 5 ml of tetrahydrofuran. The solution is stirred for 1 h in the ice bath. Then a solution of 1.5 g 5-bromo-2-chloro-benzaldehyde in 5 ml of tetrahydrofuran is added and the reaction solution is stirred for 4 h at ambient temperature. Then water is added, the mixture is extracted with ethyl acetate and the organic phase is dried over sodium sulphate. After the solvent has been eliminated the residue is purified on silica gel (cyclohexane/ethyl acetate 1:1).

Yield: 0.66 g (34% of theory)

Mass spectrum (ESI$^+$): m/z=284/286/288 (bromine+chlorine) [M]$^+$

EXAMPLE XI

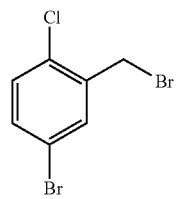

1-bromo-3-brommethyl-4-chloro-benzene 4.0 g N-bromosuccinimide are slowly added to a solution of 5.0 g 1-bromo-4-chloro-3-hydroxymethyl-benzene and 5.9 g triphenylphosphine in 50 ml of tetrahydrofuran cooled to 5° C. After 1 h stirring at ambient temperature the precipitate is filtered off and the solvent is eliminated in vacuo. The residue is purified on silica gel (cyclohexane/ethyl acetate 50:1).

Yield: 4.9 g (76% of theory)

Mass spectrum (EI): m/z=282/284/286 (Br+Cl) [M]$^+$

EXAMPLE XII

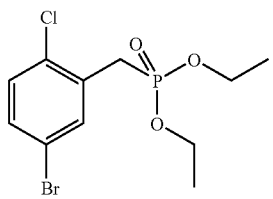

diethyl (5-bromo-2-chloro-benzyl)-phosphonate

A mixture of 9.88 g 5-bromo-2-chloro-benzylbromide in 6.10 ml triethylphosphite is stirred for 3 h at 130° C. Then a further 1.50 ml triethylphosphite are added, and the mixture is stirred for a further 3 h at 160° C. After cooling to ambient temperature the mixture is purified on silica gel (dichloromethane/methanol 1:0->9:1).

Yield: 10.66 g (90% of theory)

Mass spectrum (ESI$^+$): m/z=341/343/345 (bromine+chlorine) [M+H]$^+$

EXAMPLE XIII

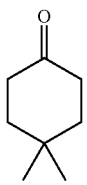

4.4-dimethylcyclohexanone 0.5 g 10% palladium on charcoal are added to a solution of 5.00 g 4,4-dimethyl-cyclohex-2-enone in 25 ml of ethyl acetate. The mixture is shaken under a hydrogen pressure of 25 psi for 3 h at ambient temperature. Then the catalyst is filtered off and the solvent is removed.

Yield: 3.38 g (67% of theory)
Mass spectrum (ESI$^+$): m/z=144 [M+NH$_4$]$^+$

EXAMPLE XIV

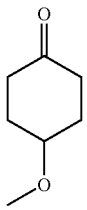

4-methoxy-cyclohexanone

A solution of 4.2 g 4-methoxycyclohexanol in 30 ml dichloromethane is added to a suspension of 52.6 g pyridinium chlorochromate on basic aluminium oxide in 90 ml dichloromethane. The suspension is stirred for 3 h at ambient temperature. Then the mixture is filtered through silica gel (dichloromethane) and the solvent is eliminated.

Yield: 3.0 g (73% of theory)

EXAMPLE XV

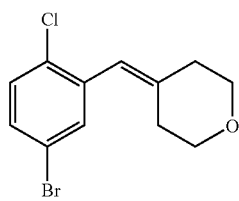

1-bromo-4-chloro-3-(tetrahydropyran-4-ylidenemethyl)-benzene

At ambient temperature a solution of 3.00 g diethyl (5-bromo-2-chloro-benzyl)-phosphonate in 10 ml of tetrahydrofuran is added dropwise to a suspension of 0.36 g sodium hydride (60% in mineral oil), which has been freed from the oil by washing with cyclohexane, in 30 ml of tetrahydrofuran. The suspension is stirred for 0.5 h at ambient temperature and then combined with 0.88 g tetrahydropyran-4-one. The mixture is stirred for 0.5 h at ambient temperature and 16 h at reflux temperature. After cooling to ambient temperature it is diluted with ethyl acetate, washed with water and the organic phase is dried with sodium sulphate. After the solvent has been eliminated the residue is purified on silica gel (cyclohexane/ethyl acetate 4:1->2:1).

Yield: 1.60 g (63% of theory)
Mass spectrum (ESI$^+$): m/z=286/288/290 (bromine+chlorine) [M]$^+$ The following compounds are obtained analogously to Example XV:

(1) 1-bromo-4-chloro-3-(4,4-dimethyl-cyclohexylidenemethyl)-benzene

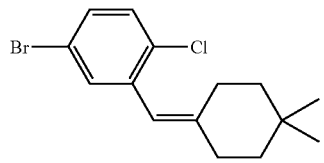

(2) 1-bromo-4-chloro-3-(4-methoxy-cyclohexylidenemethyl)-benzene

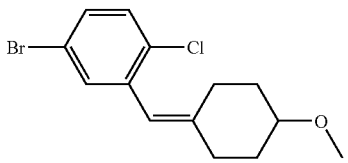

(3) 1-bromo-4-chloro-3-(adamantylidenemethyl)-benzene

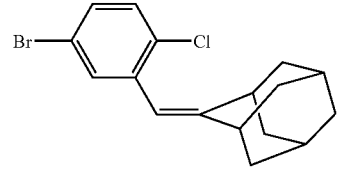

Mass spectrum (EI): m/z=336/338/340 (bromine and chlorine) [M$^+$]

EXAMPLE XVI

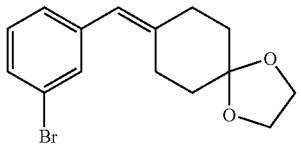

8-(3-bromo-benzylidene)-1,4-dioxo-spiro[4.5]decane

A solution of 8.0 g 3-bromobenzylbromide and 8.4 g triphenylphosphine in 100 ml of toluene is refluxed for 12 h with stirring. Then the precipitate formed is filtered off, washed with toluene and dried at 50° C. The dried 3-bromobenzyl-triphenylphosphonium bromide is added to an ice-cooled suspension of 1.64 g sodium hydride (60% in mineral oil) in 50 ml dry tetrahydrofuran and the resulting reaction mixture is stirred for 1 h at 45° C. Then at ambient temperature 5.4 g 1,4-dioxo-spiro[4.5]decan-8-one are added and the reaction solution is stirred for 12 h at ambient temperature. Then water is added, the organic phase is separated off, the aqueous phase is extracted with dichloromethane, and the combined organic phases are dried over sodium sulphate. After the solvent has been eliminated the residue is purified on silica gel (cyclohexane/ethyl acetate 1:0->7:3).

Yield: 3.35 g (31% of theory)

Mass spectrum (ESI+): m/z=308/310 (bromine) [M]+

EXAMPLE XVII

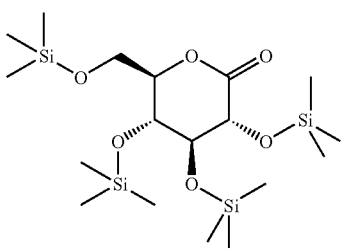

2,3,4,6-tetrakis-O-(trimethylsilyl)-D-glucopyranone

A solution of 20 g of D-glucono-1,5-lactone and 98.5 ml N-methylmorpholine in 200 ml of tetrahydrofuran is cooled to −5° C. Then 85 ml trimethylsilyl chloride are added dropwise in such a way that the temperature does not exceed 5° C. The solution is then stirred for 1 h at ambient temperature, for 5 h at 35° C. and for a further 14 h at ambient temperature. After the addition of 300 ml of toluene the solution is cooled in the ice bath, and 500 ml of water are added so that the temperature does not exceed 10° C. The organic phase is then separated off and washed once each with aqueous sodium dihydrogen phosphate solution, water and saturated aqueous sodium chloride solution. The solvent is removed, the residue is taken up in 250 ml of toluene and the solvent is again eliminated totally.

Yield: 52.5 g (approx. 90% pure)

Mass spectrum (ESI+): m/z=467 [M+H]+

EXAMPLE XVIII

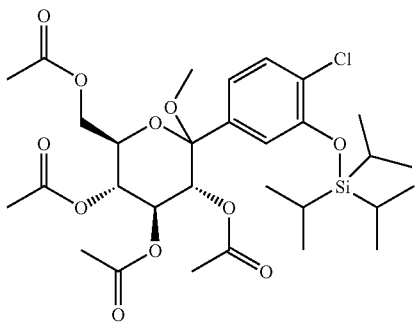

1-chloro-4-(2,3,4,6-tetra-O-acetyl-1-methoxy-D-glucopyranos-1-yl)-2-(tri-isopropyl-silyloxy)-benzene A solution of 5.0 g 1-bromo-4-chloro-3-(tri-isopropyl-silyloxy)-benzene in 60 ml dry diethyl ether is cooled to −80° C. under argon. 17.7 ml of a 1.7 M solution of tert-butyl-lithium in pentane are added dropwise to the cooled solution. The solution is stirred for 30 min at −80° C. and then added dropwise through a pressure needle to a solution of 7.3 g 2,3,4,6-tetrakis-O-(trimethylsilyl)-D-glucopyranone in 40 ml diethyl ether cooled to −80° C. The resulting solution is stirred for 4 h at −78° C. Then a solution of 3 ml methanesulphonic acid in 80 ml of methanol is added and the solution is stirred for 16 h at ambient temperature. The solution is then neutralised with ethyldiisopropylamine and evaporated down. The residue is taken up in toluene and evaporated down again. Then the residue is dissolved in 36 ml of toluene and 3.4 ml ethyldiisopropylamine are added to the solution. The solution is cooled in the ice bath and then 6.3 ml acetic anhydride and 0.17 g 4-dimethylaminopyridine are added. The solution is stirred for 6 h at ambient temperature and then combined with aqueous sodium hydrogen carbonate solution. The organic phase is separated off and the aqueous phase is extracted with ethyl acetate. After drying the combined organic extracts through sodium sulphate and eliminating the solvent the residue is chromatographed on silica gel (cyclohexane/ethyl acetate 6:1->1:1).

Yield: 5.8 g (65% of theory)

Mass spectrum (ESI+): m/z=662/664 (chlorine) [M+NH4]+

The following compounds are obtained analogously to Example XVIII:

(1) 1-chloro-4-(2,3,4,6-tetra-O-acetyl-1-methoxy-D-glucopyranos-1-yl)-2-(cis-4-methoxy-cyclohexyloxy)-benzene

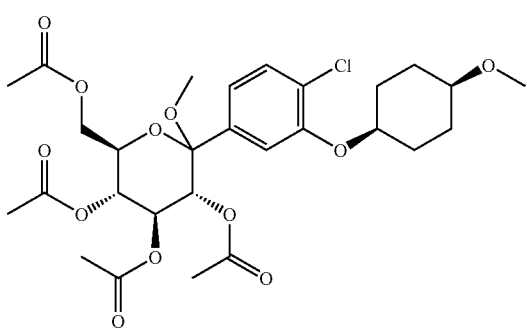

Mass spectrum (ESI$^+$): m/z=618/620 (chlorine) [M+NH$_4$]$^+$ (2) 1-chloro-4-(2,3,4,6-tetra-O-acetyl-1-methoxy-D-glucopyranos-1-yl)-2-(trans-4-methoxy-cyclohexyloxy)-benzene

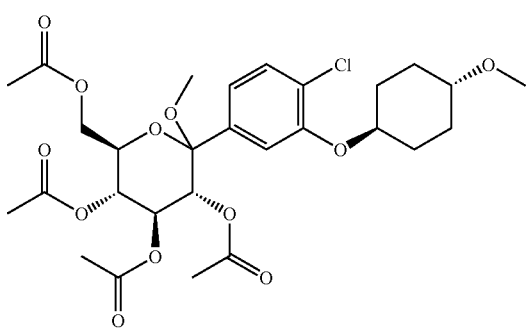

Mass spectrum (ESI$^+$): m/z=618/620 (chlorine) [M+NH$_4$]$^+$ (3) 1-chloro-4-(2,3,4,6-tetra-O-acetyl-1-methoxy-D-glucopyranos-1-yl)-2-cyclohexylidenemethyl-benzene

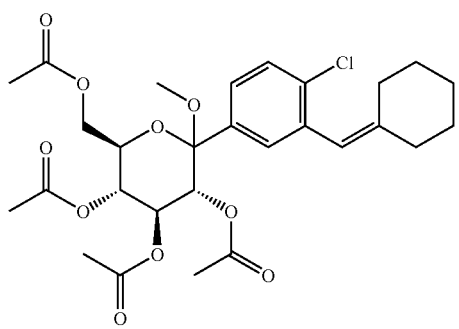

Mass spectrum (ESI$^+$): m/z=584/586 (chlorine) [M+NH$_4$]$^+$ (4) 1-(2,3,4,6-tetra-O-acetyl-1-methoxy-D-glucopyranos-1-yl)-3-(4,4-dimethoxy-cyclohexylidenemethyl)-benzene starting from 8-(3-bromo-benzylidene)-1,4-dioxo-spiro[4.5]decane

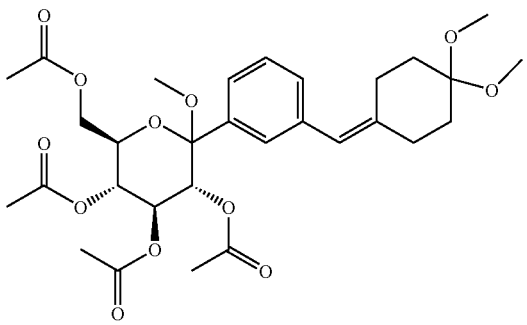

Mass spectrum (ESI$^+$): m/z=610 [M+NH$_4$]$^+$ (5) 1-chloro-2-(4,4-dimethylcyclohexyloxy)-4-(2,3,4,6-tetra-O-acetyl-1-methoxy-D-glucopyranos-1-yl)-benzene

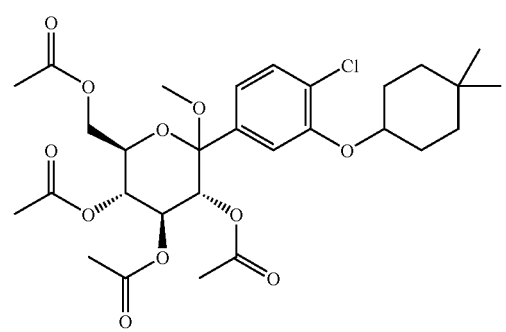

Mass spectrum (ESI$^+$): m/z=616/618 (chlorine) [M+NH$_4$]$^+$ (6) 1-chloro-2-(1,2,3,4-tetrahydronaphth-2-yloxy)-4-(2,3,4,6-tetra-O-acetyl-1-methoxy-D-glucopyranos-1-yl)-benzene

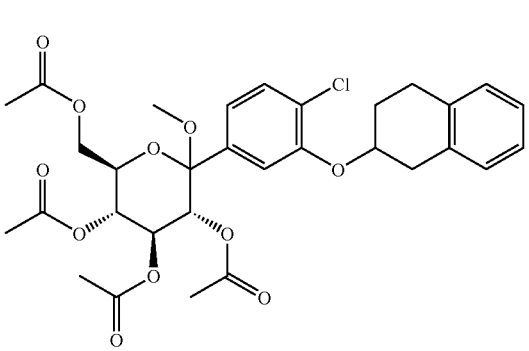

Mass spectrum (ESI$^+$): m/z=636/638 (chlorine) [M+NH$_4$]$^+$ (7) 1-chloro-2-(tetrahydropyran-4-yloxy)-4-(2,3,4,6-tetra-O-acetyl-1-methoxy-D-glucopyranos-1-yl)-benzene

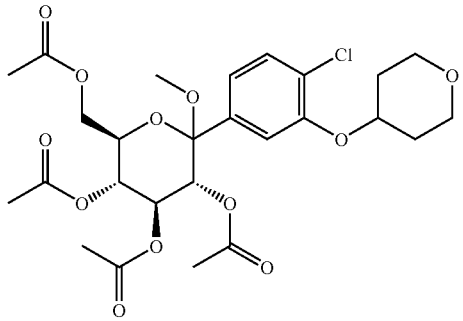

Mass spectrum (ESI$^+$): m/z=590/592 (chlorine) [M+NH$_4$]$^+$ (8) 1-chloro-2-(cis-3-methoxy-cyclopent-1-yloxy)-4-(2,3,4,6-tetra-O-acetyl-1-methoxy-D-glucopyranos-1-yl)-benzene

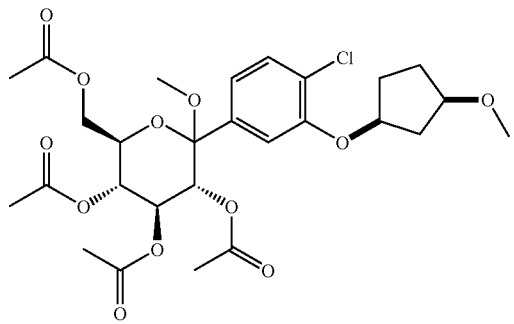

Mass spectrum (ESI$^+$): m/z=604/606 (chlorine) [M+NH$_4$]$^+$ (9) 1-chloro-4-(2,3,4,6-tetra-O-acetyl-1-methoxy-D-glucopyranos-1-yl)-2-(tetrahydropyran-4-ylidenemethyl)-benzene

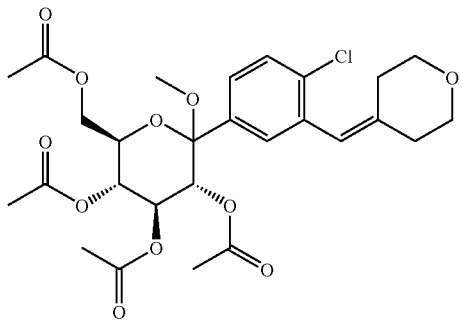

Mass spectrum (ESI$^+$): m/z=586/588 (chlorine) [M+NH$_4$]$^+$

(10) 1-chloro-4-(2,3,4,6-tetra-O-acetyl-1-methoxy-D-glucopyranos-1-yl)-2-(4,4-dimethyl-cyclohexylidenemethyl)-benzene

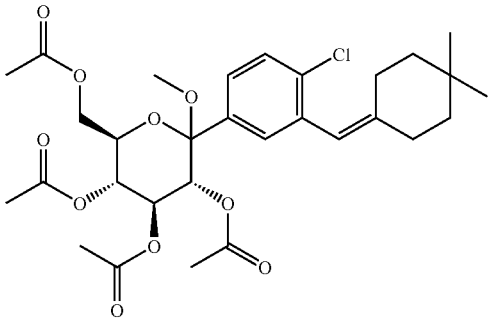

Mass spectrum (ESI$^+$): m/z=612/614 (chlorine) [M+NH$_4$]$^+$

(11) 1-chloro-4-(2,3,4,6-tetra-O-acetyl-1-methoxy-D-glucopyranos-1-yl)-2-(4-methoxy-cyclohexylidenemethyl)-benzene

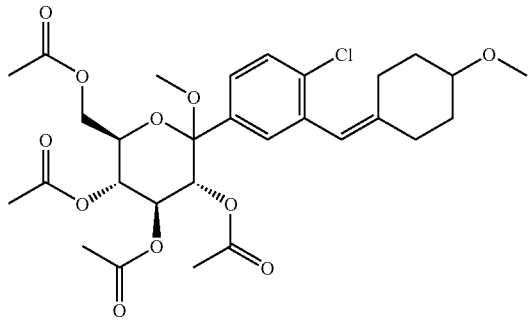

Mass spectrum (ESI$^+$): m/z=614/616 (chlorine) [M+NH$_4$]$^+$

(12) 1-chloro-4-(2,3,4,6-tetra-O-acetyl-1-methoxy-D-glucopyranos-1-yl)-2-(adamantylidenemethyl)-benzene

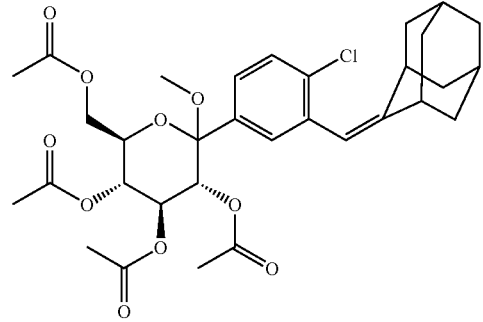

Mass spectrum (ESI$^+$): m/z=636/638 (chlorine) [M+NH$_4$]$^+$

EXAMPLE XIX

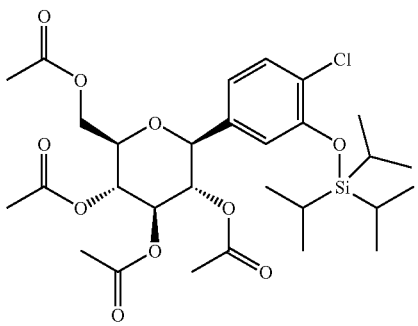

1-chloro-4-(2,3,4,6-tetra-O-acetyl-β-D-glucopyranos-1-yl)-2-(tri-isopropyl-silyloxy)-benzene A solution of 5.83 g 1-chloro-4-(2,3,4,6-tetra-O-acetyl-1-methoxy-D-glucopyranos-1-yl)-2-(tri-isopropyl-silyloxy)-benzene in 100 ml acetonitrile and 0.22 ml of water is cooled in the ice bath. Then 7 ml triethylsilane and 1.5 ml boron trifluoride etherate are added. The solution is stirred for 1 h in the ice bath and then at ambient temperature. After 5 h a further 6 ml triethylsilane and 1.2 ml boron trifluoride etherate are added. After another 5 h stirring at ambient temperature aqueous sodium hydrogen carbonate solution is added, the mixture is stirred for 0.5 h and then extracted with ethyl acetate. The organic phase is dried over sodium sulphate and evaporated to dryness.

Yield: 4.80 g (86% of theory)

Mass spectrum (ESI$^+$): m/z=637/639 (chlorine) [M+Na]$^+$

The following compounds are obtained analogously to Example XIX:

(1) 1-chloro-4-(2,3,4,6-tetra-O-acetyl-β-D-glucopyranos-1-yl)-2-(cis-4-methoxy-cyclohexyloxy)-benzene

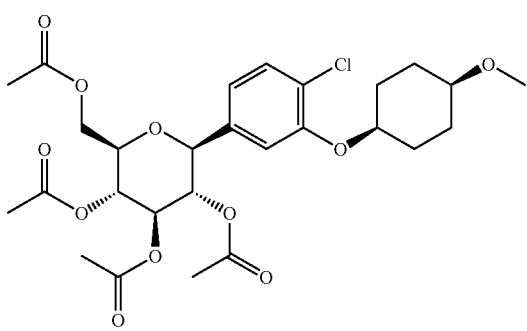

Mass spectrum (ESI$^+$): m/z=589/591 (chlorine) [M+NH$_4$]$^+$ (2) 1-chloro-4-(2,3,4,6-tetra-O-acetyl-β-D-glucopyranos-1-yl)-2-(trans-4-methoxy-cyclohexyloxy)-benzene

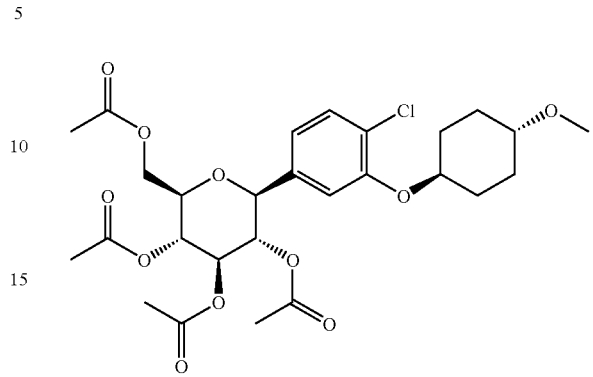

Mass spectrum (ESI$^+$): m/z=589/591 (chlorine) [M+NH$_4$]$^+$ (3) 1-chloro-4-(2,3,4,6-tetra-O-acetyl-β-D-glucopyranos-1-yl)-2-cyclohexylidenemethyl-benzene

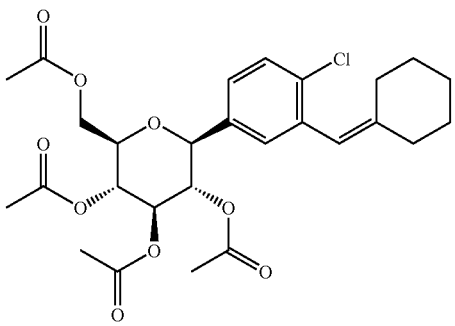

Mass spectrum (ESI$^+$): m/z=559/561 (chlorine) [M+Na]$^+$ (4) 1-(2,3,4,6-tetra-O-acetyl-β-D-glucopyranos-1-yl)-2-(4-methoxy-cyclohexylidenemethyl)-benzene starting from 1-(2,3,4,6-tetra-O-acetyl-1-methoxy-D-glucopyranos-1-yl)-3-(4,4-dimethoxy-cyclohexylidenemethyl)-benzene

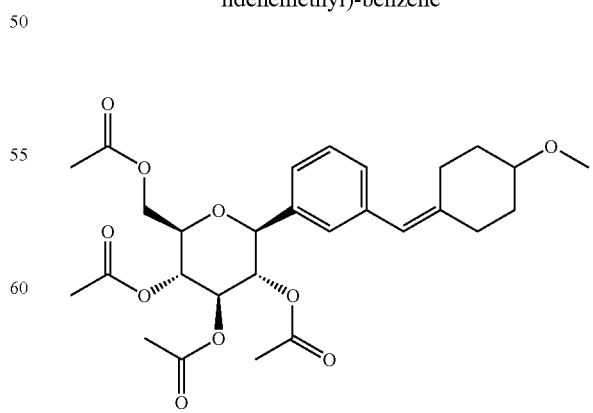

Mass spectrum (ESI$^+$): m/z=550 [M+NH$_4$]$^+$ (5) 1-(2,3,4,6-tetra-O-acetyl-β-D-glucopyranos-1-yl)-2-(4-hydroxy-cyclohexylidenemethyl)-benzene as a by-product in the synthesis of Example XIX (4) starting from 1-(2,3,4,6-tetra-O-acetyl-1-methoxy-D-glucopyranos-1-yl)-3-(4,4-dimethoxy-cyclohexylidenemethyl)-benzene

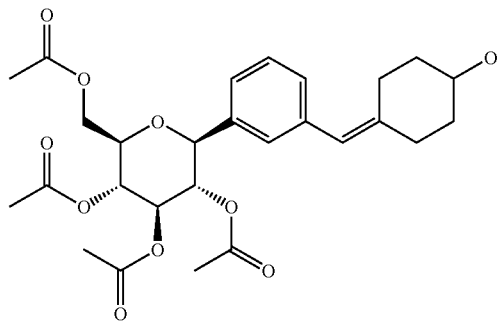

Mass spectrum (ESI⁺): m/z=566 (chlorine) [M+NH₄]⁺

(6) 1-chloro-2-(4,4-dimethylcyclohexyloxy)-4-(2,3,4,6-tetra-O-acetyl-β-D-glucopyranos-1-yl)-benzene

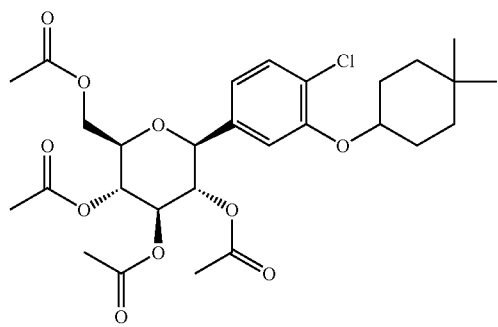

This compound was deacetylated directly to form the end product without any further characterisation.

(7) 1-chloro-2-(1,2,3,4-tetrahydronaphth-2-yloxy)-4-(2,3,4,6-tetra-O-acetyl-β-D-glucopyranos-1-yl)-benzene

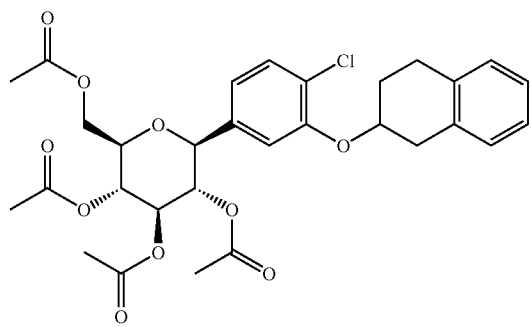

This compound was deacetylated directly to form the end product without any further characterisation.

(8) 1-chloro-2-(tetrahydropyran-4-yloxy)-4-(2,3,4,6-tetra-O-acetyl-β-D-glucopyranos-1-yl)-benzene

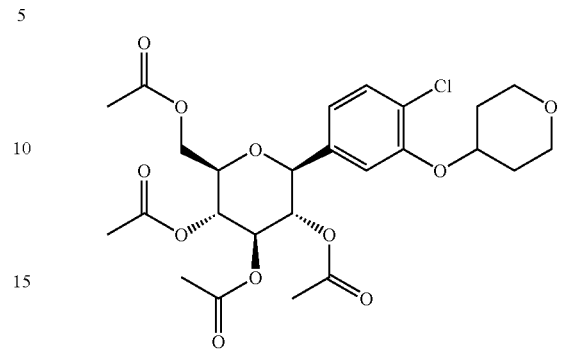

This compound was deacetylated directly to form the end product without any further characterisation.

(9) 1-chloro-2-(cis-3-methoxy-cyclopentyl-1-yloxy)-4-(2,3,4,6-tetra-O-acetyl-β-D-glucopyranos-1-yl)-benzene

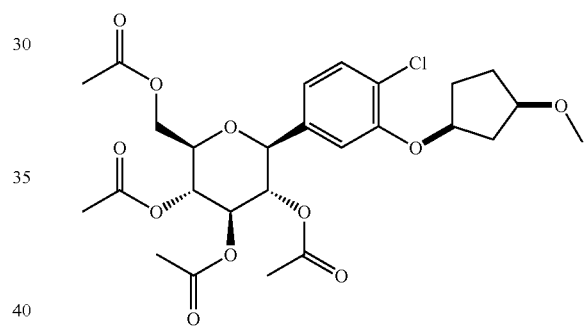

This compound was deacetylated directly to form the end product without any further characterisation.

(10) 1-chloro-4-(2,3,4,6-tetra-O-acetyl-β-D-glucopyranos-1-yl)-2-(tetrahydropyran-4-ylidenemethyl)-benzene

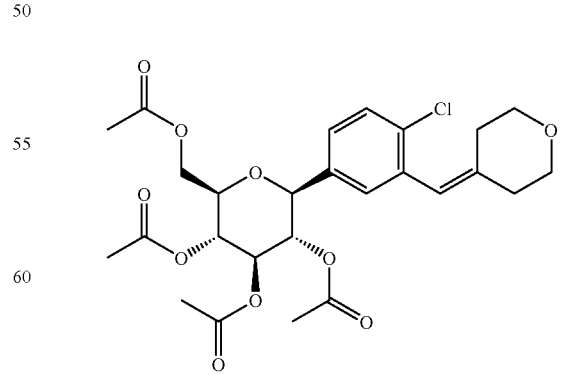

This compound was deacetylated directly to form the end product without any further characterisation.

(11) 1-chloro-4-(2,3,4,6-tetra-O-acetyl-β-D-glucopyranos-1-yl)-2-(4,4-dimethyl-cyclohexylidenemethyl)-benzene

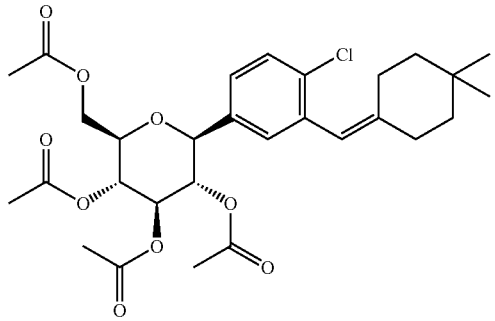

This compound was deacetylated directly to form the end product without any further characterisation.

(12) 1-chloro-4-(2,3,4,6-tetra-O-acetyl-β-D-glucopyranos-1-yl)-2-(4-methoxy-cyclohexylidenemethyl)-benzene

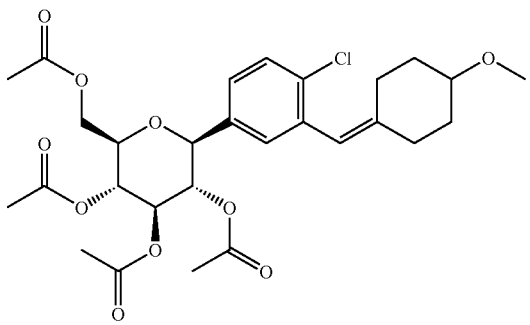

This compound was deacetylated directly to form the end product without any further characterisation.

(13) 1-chloro-4-(2,3,4,6-tetra-O-acetyl-β-D-glucopyranos-1-yl)-2-(adamantylidenemethyl)-benzene

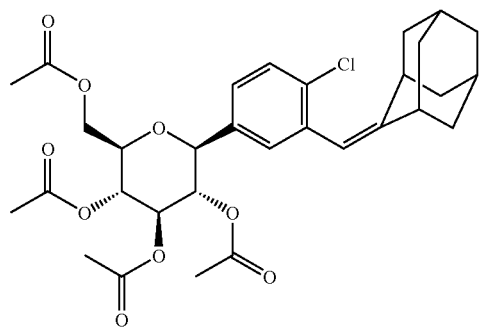

This compound was deacetylated directly to form the end product without any further characterisation.

EXAMPLE XX

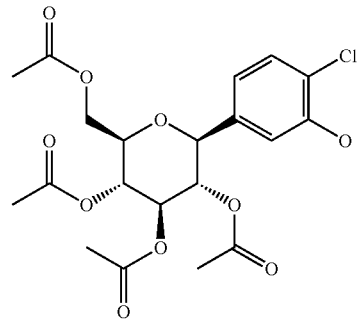

1-chloro-4-(2,3,4,6-tetra-O-acetyl-β-D-glucopyranos-1-yl)-2-hydroxy-benzene 5 ml of a 1 M solution of tetrabutylammonium fluoride in tetrahydrofuran are added to an ice-cooled solution of 4.80 g 1-chloro-4-(2,3,4,6-tetra-O-acetyl-β-D-glucopyranos-1-yl)-2-(tri-isopropyl-silyloxy)-benzene in 25 ml dry tetrahydrofuran. The solution is stirred for 14 h at ambient temperature and then combined with water. It is extracted with ethyl acetate, dried over sodium sulphate and the solvent is removed. The residue is stirred in cyclohexane/ethyl acetate (5:1) and then dried.

Yield: 1.70 g (86% of theory) Mass spectrum (ESI$^+$): m/z=476/478 (chlorine) [M+NH$_4$]$^+$

EXAMPLE XXI

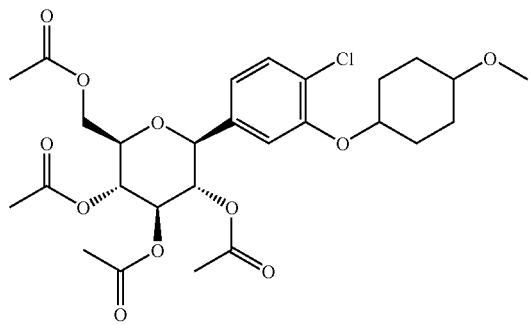

1-chloro-4-(2,3,4,6-tetra-O-acetyl-β-D-glucopyranos-1-yl)-2-(4-methoxy-cyclohexyloxy)-benzene 0.08 g 4-methoxycyclohexanol, 0.16 g triphenylphosphine and 0.12 ml diisopropyl azodicarboxylate are added to a solution of 0.25 g 1-chloro-4-(2,3,4,6-tetra-O-acetyl-β-D-glucopyranos-1-yl)-2-hydroxy-benzene in 3 ml of tetrahydrofuran, in the order stated. The solution is stirred for 14 h at ambient temperature and then combined with aqueous potassium carbonate solution. Then it is extracted with ethyl acetate, dried over sodium sulphate and the solvent is removed. The residue is purified on silica gel (cyclohexane/ethyl acetate 7:3->1:1).

Yield: 0.05 g (16% of theory)

Preparation of the End Compounds

EXAMPLE 1

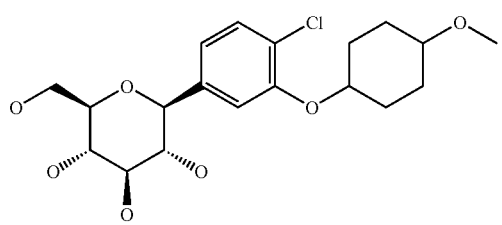

1-chloro-4-(β-D-glucopyranos-1-yl)-2-(4-methoxy-cyclohexyloxy)-benzene 0.13 ml of 4M potassium hydroxide solution are added to a solution of 0.05 g 1-chloro-4 -(2,3,4,6-tetra-O-acetyl-β-D-glucopyranos-1-yl)-2-(4-methoxy-benzyl)-benzene in 3 ml of methanol. The solution is stirred for 3 h at ambient temperature and then neutralised with 1 M hydrochloric acid. The solution is freed from methanol, combined with aqueous sodium chloride solution and extracted with ethyl acetate. The organic phase is dried over sodium sulphate and the solvent is removed. The residue is purified on silica gel (dichloromethane/methanol 1:0->3:1).

Yield: 0.01 g (28% of theory)

Mass spectrum (ESI$^+$): m/z=420/422 (chlorine) [M+NH$_4$]$^+$

The following compounds are obtained analogously to Example 1:

(1) 1-chloro-4-(β-D-glucopyranos-1-yl)-2-(cis-4-methoxy-cyclohexyloxy)-benzene

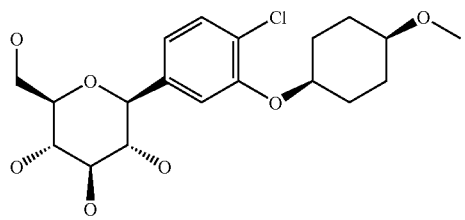

Mass spectrum (ESI$^+$): m/z=403/405 (chlorine) [M+H]$^+$ (2) 1-chloro-4-(β-D-glucopyranos-1-yl)-2-(trans-4-methoxy-cyclohexyloxy)-benzene

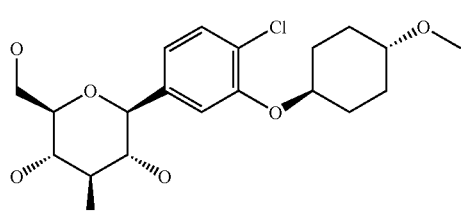

Mass spectrum (ESI$^+$): m/z=420/422 (chlorine) [M+NH$_4$]$^+$ (3) 1-chloro-4-(β-D-glucopyranos-1-yl)-2-cyclohexylidenemethyl-benzene

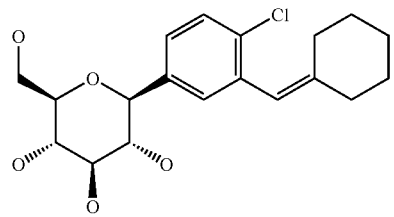

Mass spectrum (ESI$^+$): m/z=386/388 (chlorine) [M+NH$_4$]$^+$ (4) 1-(β-D-glucopyranos-1-yl)-3-(4-methoxy-cyclohexylmethyl)-benzene starting from 1-(2,3,4,6-tetra-O-acetyl-β-D-glucopyranos-1-yl)-3-(4-methoxy-cyclohexylmethyl)-benzene [see Example 2(1)]

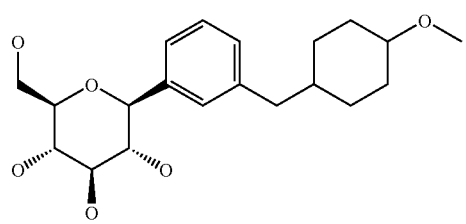

Mass spectrum (ESI$^+$): m/z=367 [M+H]$^+$ (5) 1-(β-D-glucopyranos-1-yl)-3-(4-hydroxy-cyclohexylidenemethyl)-benzene

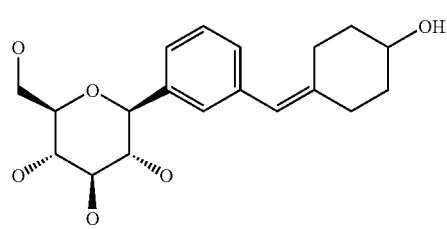

Mass spectrum (ESI$^+$): m/z=368 [M+NH$_4$]$^+$ (6) 1-chloro-2-(4,4-dimethylcyclohexyloxy)-4-(β-D-glucopyranos-1-yl)-benzene

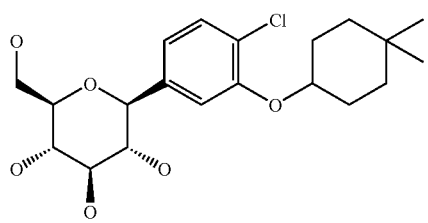

Mass spectrum (ESI$^+$): m/z=418/420 (chlorine) [M+NH$_4$]$^+$ (7) 1-chloro-2-(1,2,3,4-tetrahydronaphth-2-yloxy)-4-(β-D-glucopyranos-1-yl)-benzene

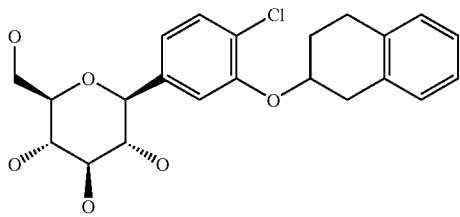

Mass spectrum (ESI⁺): m/z=438/440 (chlorine) [M+NH$_4$]⁺

(8) 1-chloro-2-(tetrahydropyran-4-yloxy)-4-(β-D-glucopyranos-1-yl)-benzene

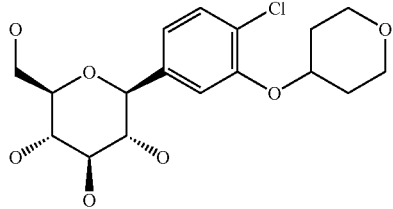

Mass spectrum (ESI⁺): m/z=392/394 (chlorine) [M+NH$_4$]⁺

(9) 1-chloro-2-(cis-3-methoxycyclopent-1-yloxy)-4-(β-D-glucopyranos-1-yl)-benzene

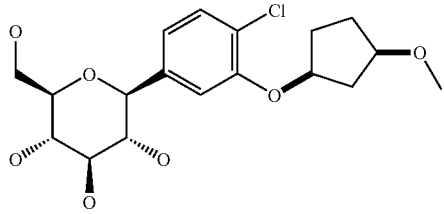

Mass spectrum (ESI⁺): m/z=389/391 (chlorine) [M+H]⁺

(10) 1-chloro-4-(β-D-glucopyranos-1-yl)-2-(tetrahydropyran-4-ylidenemethyl)-benzene

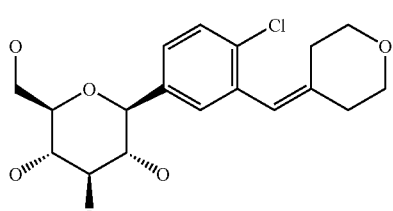

Mass spectrum (ESI⁺): m/z=388/390 (chlorine) [M+NH$_4$]⁺

(11) 1-chloro-4-(β-D-glucopyranos-1-yl)-2-(4,4-dimethyl-cyclohexylidenemethyl)-benzene

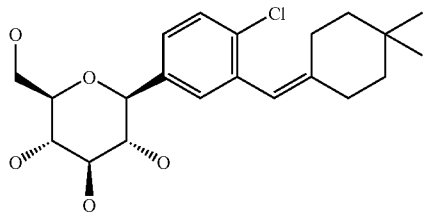

Mass spectrum (ESI⁺): m/z=414/416 (chlorine) [M+NH$_4$]⁺

(12) 1-chloro-4-(β-D-glucopyranos-1-yl)-2-(4-methoxy-cyclohexylidenemethyl)-benzene

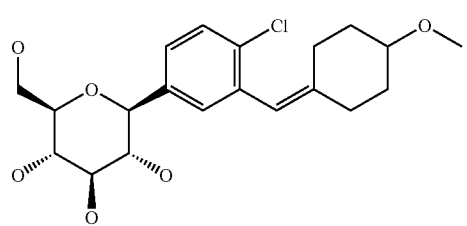

Mass spectrum (ESI⁺): m/z=399/401 (chlorine) [M+H]⁺

(13) 1-chloro-2-(adamantylidenemethyl)-(4-β-D-glucopyranos-1-yl)-benzene

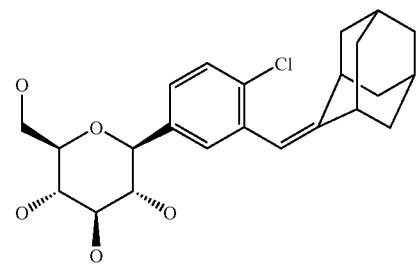

Mass spectrum (ESI⁺): m/z=438/440 (chlorine) [M+NH$_4$]⁺

EXAMPLE 2

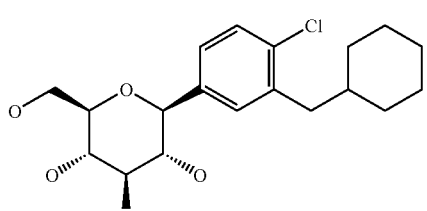

1-chloro-4-(β-D-glucopyranos-1-yl)-2-cyclohexylmethyl-benzene 40 mg of 10% palladium on charcoal are added to a solution of 0.10 g 1-chloro-4-β-D-glucopyranos-1-yl-2-cyclohexylidenemethyl-benzene in 5 ml of ethyl acetate. The solution is stirred for 1 h under a hydrogen atmosphere (1 atm) at ambient temperature. Then the catalyst is filtered off, the filtrate is evaporated down and the residue is chromatographed on silica gel (dichloromethane/methanol 4:1).

Yield: 0.07 g (70% of theory)

Mass spectrum (ESI$^+$): m/z=388/390 (chlorine) [M+NH$_4$]$^+$

The following compounds are obtained analogously to Example 2:

(1) 1-(2,3,4,6-tetra-O-acetyl-β-D-glucopyranos-1-yl)-3-(4-methoxy-cyclohexylmethyl)-benzene

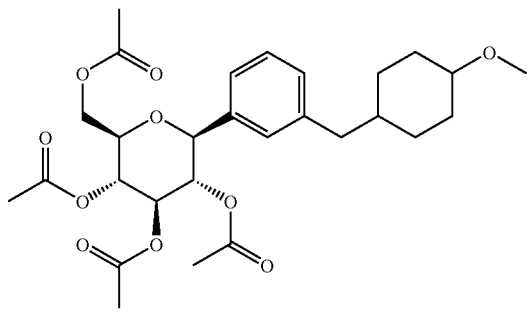

Mass spectrum (ESI$^+$): m/z=535 [M+H]$^+$ (2) 1-(β-D-glucopyranos-1-yl)-3-(4-hydroxy-cyclohexylmethyl)-benzene

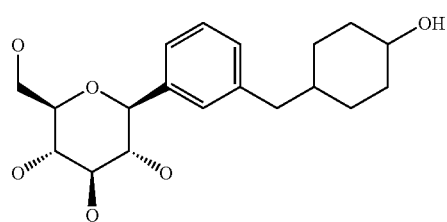

Mass spectrum (ESI$^+$): m/z=370 [M+NH$_4$]$^+$ (3) 1-chloro-2-(tetrahydropyran-4-ylmethyl)-4-(β-D-glucopyranos-1-yl)-benzene

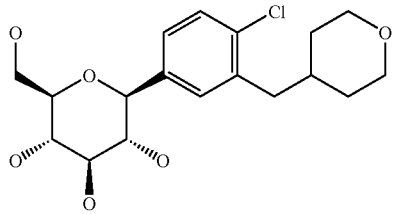

Mass spectrum (ESI$^+$): m/z=390/392 (chlorine) [M+NH$_4$]$^+$ (4) 1-chloro-2-(4,4-dimethyl-cyclohexylmethyl)-4-(β-D-glucopyranos-1-yl)-benzene

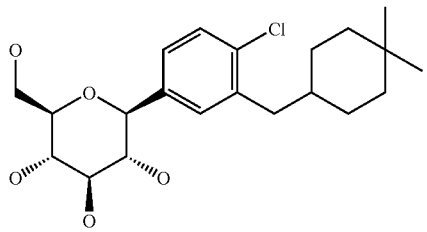

Mass spectrum (ESI$^+$): m/z=416/418 (chlorine) [M+NH$_4$]$^+$ (5) 1-chloro-2-(4-methoxy-cyclohexylmethyl)-4-(β-D-glucopyranos-1-yl)-benzene

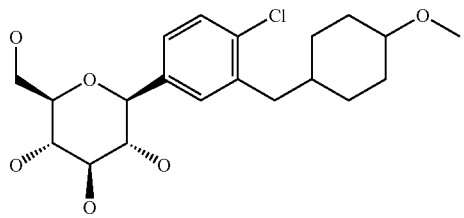

Mass spectrum (ESI$^+$): m/z=418/420 (chlorine) [M+NH$_4$]$^+$ (6) 1-chloro-2-(adamant-2-ylmethyl)-4-(β-D-glucopyranos-1-yl)-benzene

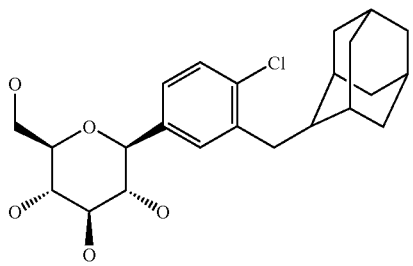

Mass spectrum (ESI$^+$): m/z=440/442 (chlorine) [M+NH$_4$]$^+$

The following compounds are also prepared analogously to the foregoing Examples and other methods known from the literature:

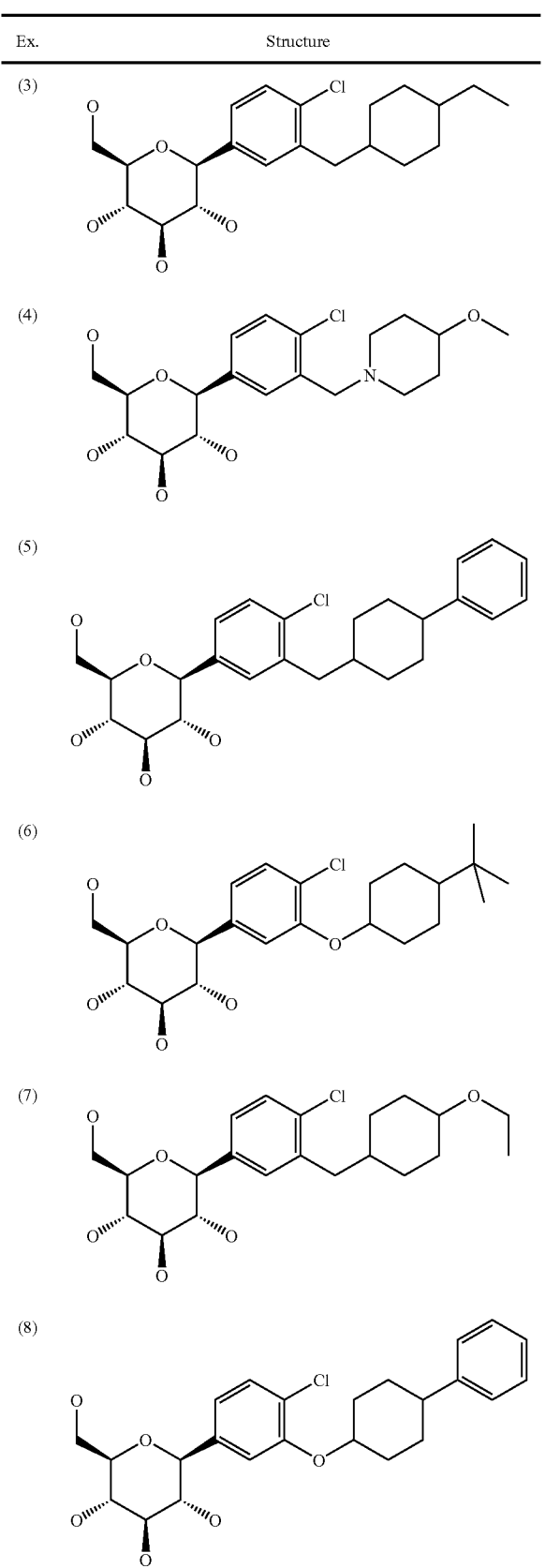
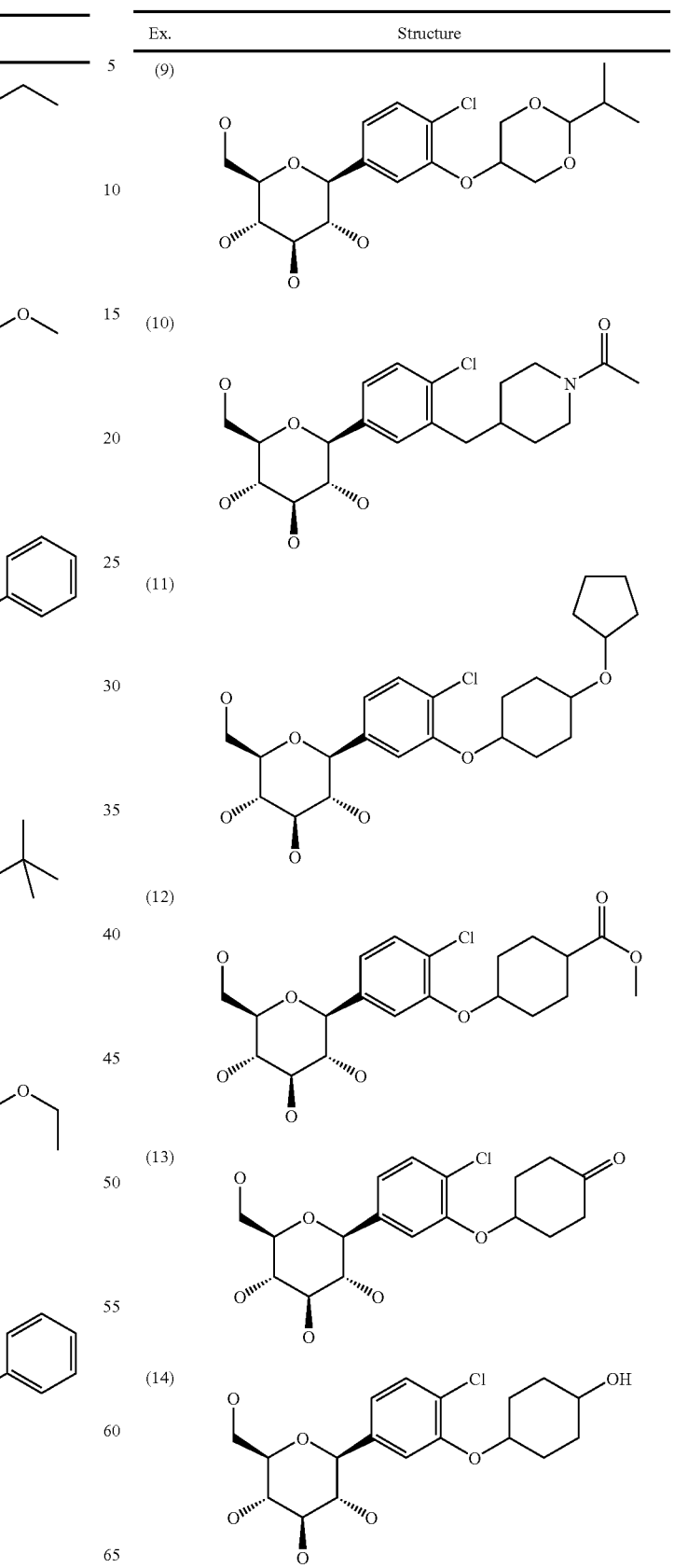

-continued
| Ex. | Structure |
|---|---|
| (15) | 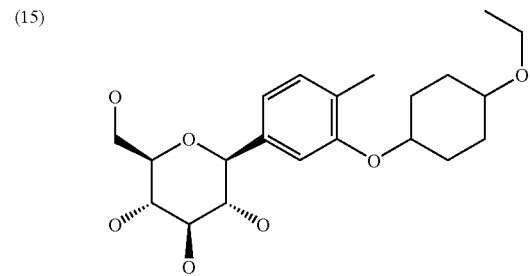 |
| (16) | 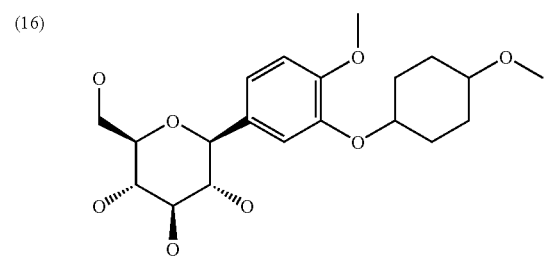 |
| (17) | 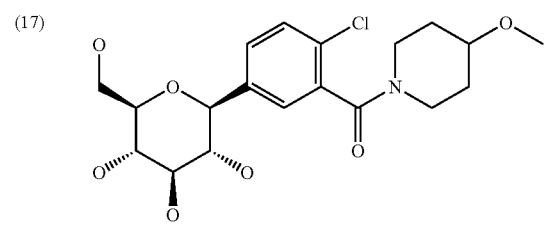 |
| (18) | 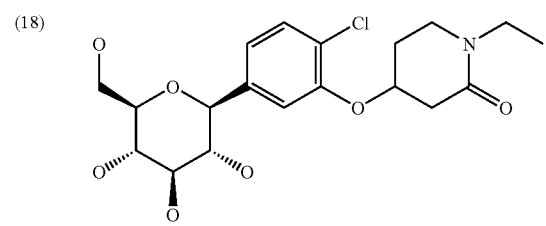 |
| (19) | 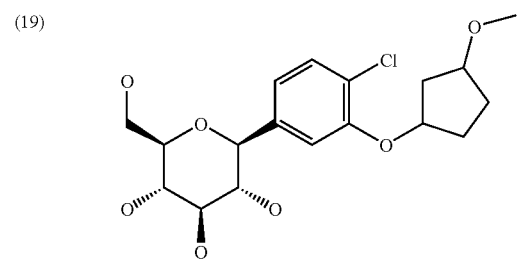 |
| (20) | 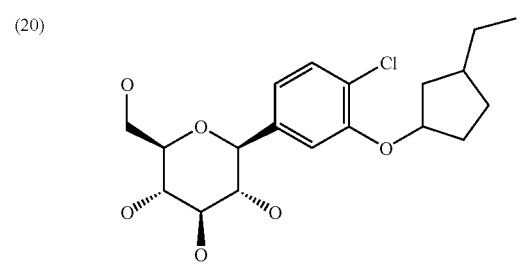 |
-continued
| Ex. | Structure |
|---|---|
| (21) | 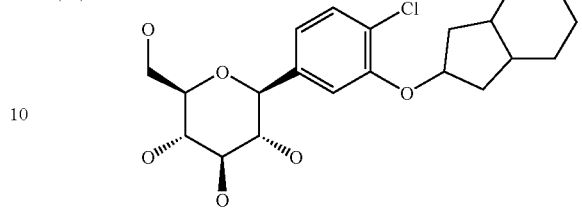 |
| (22) | 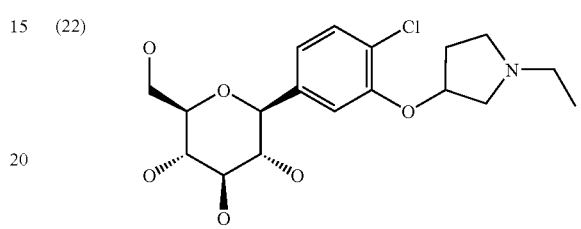 |
| (23) | 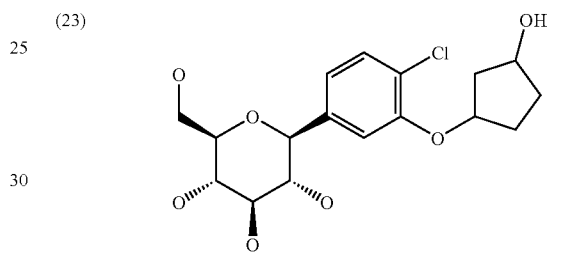 |
| (24) | 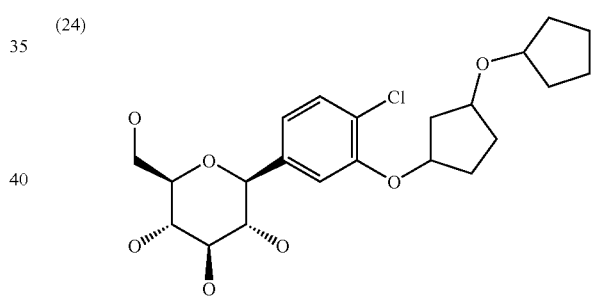 |
| (25) | 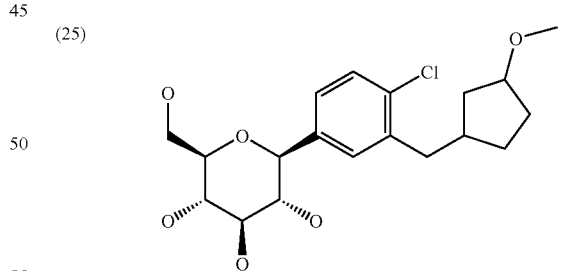 |
| (26) | 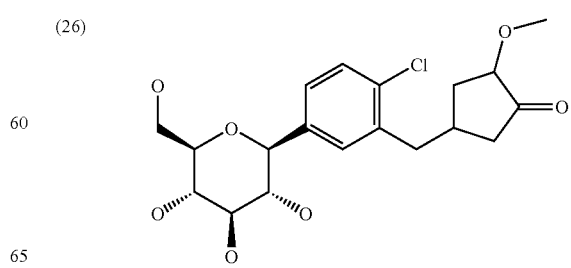 |

-continued

| Ex. | Structure |
|---|---|
| (27) | 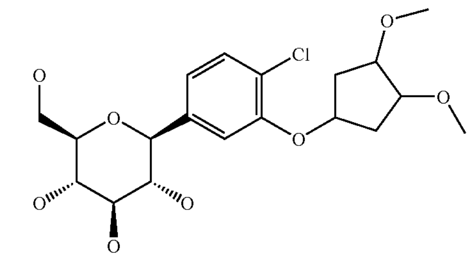 |
| (28) | 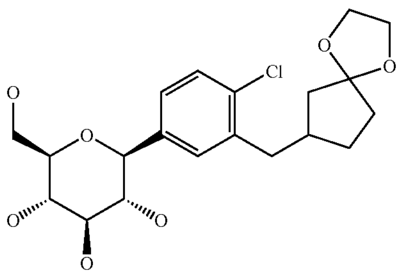 |
| (29) | 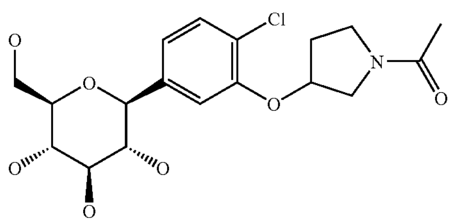 |
| (30) | 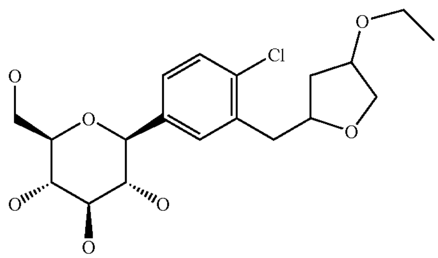 |
| (31) | 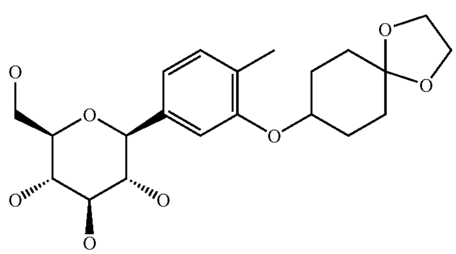 |
| (32) | 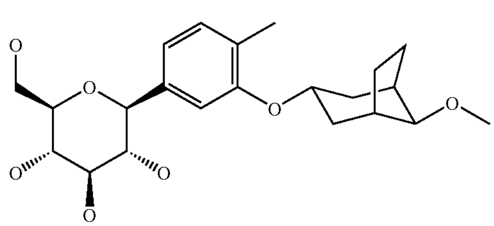 |

-continued

| Ex. | Structure |
|---|---|
| (33) | 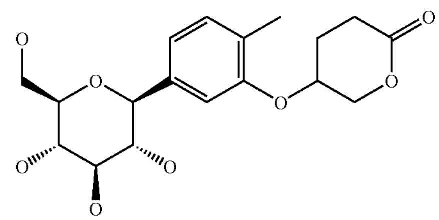 |
| (34) | 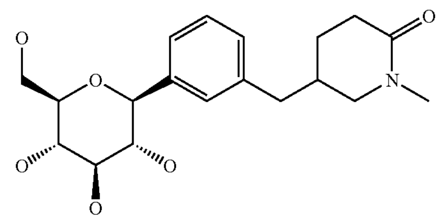 |
| (35) | 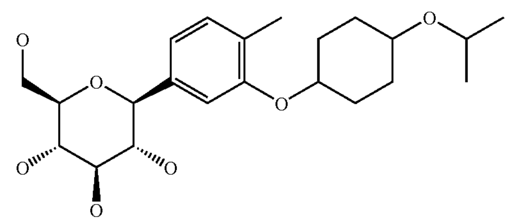 |
| (36) | 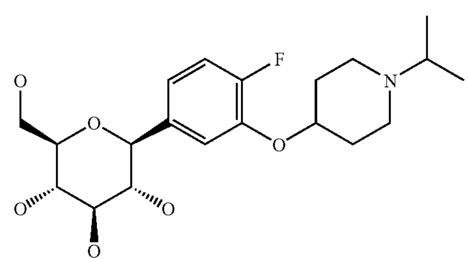 |
| (37) | 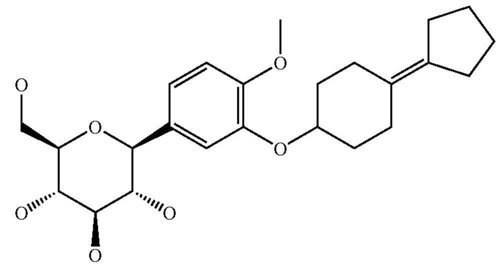 |
| (38) | 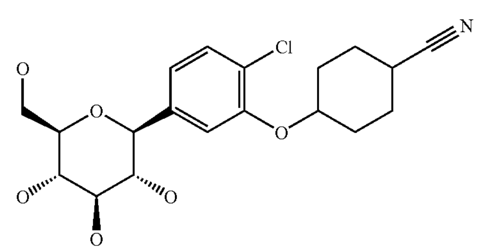 |

-continued
| Ex. | Structure |
|---|---|
| (39) | 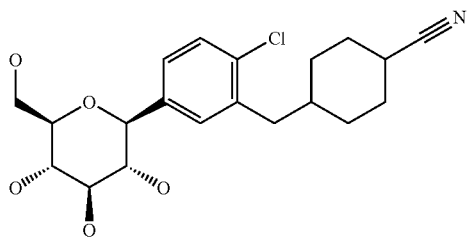 |
| (40) | 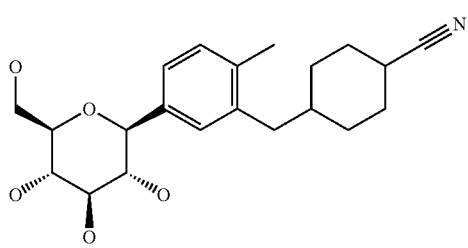 |
| (41) | 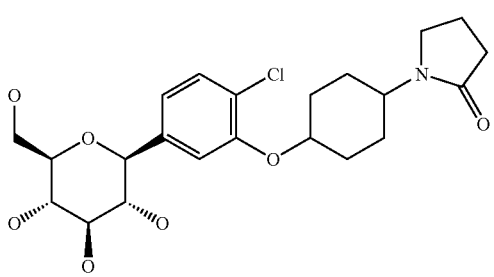 |
| (42) | 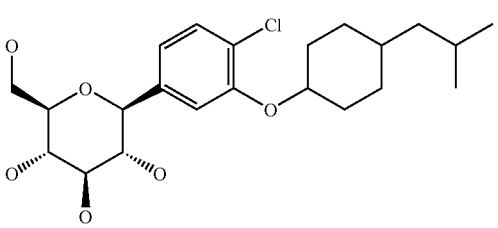 |
| (43) | 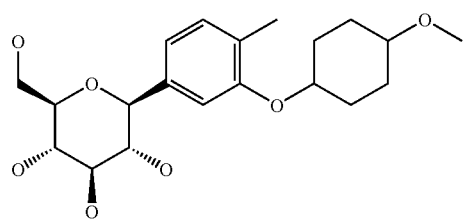 |
| (44) | 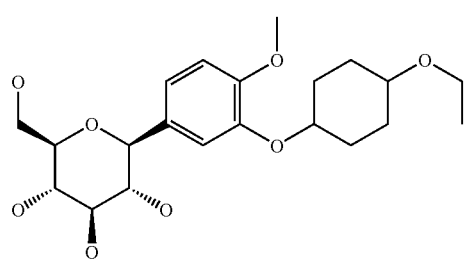 |
-continued
| Ex. | Structure |
|---|---|
| (45) | 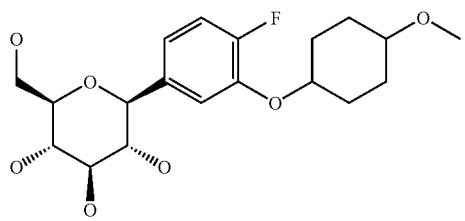 |
| (46) | 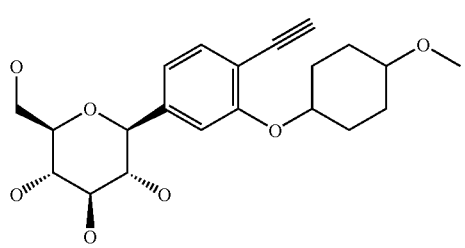 |
| (47) | 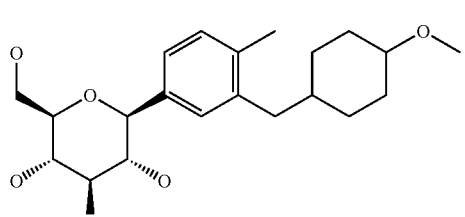 |
| (48) | 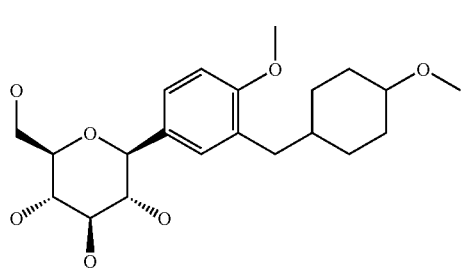 |
| (49) | 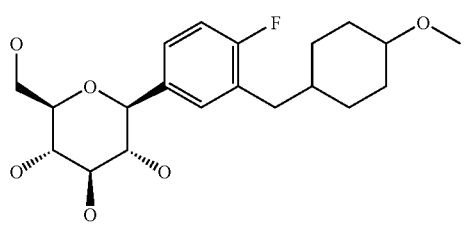 |
| (50) | 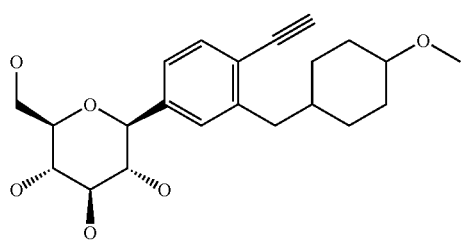 |

| Ex. | Structure |
|---|---|
| (51) | 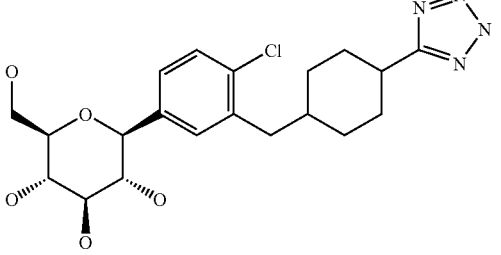 |
| (52) | 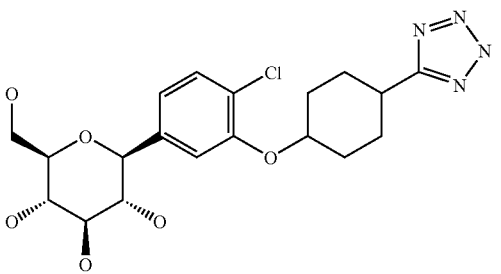 |
| (53) | 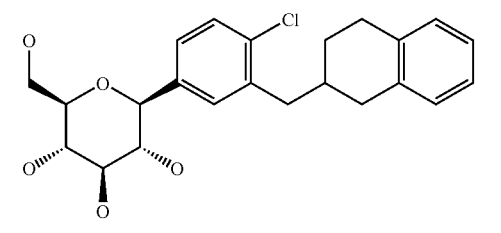 |
| (54) | 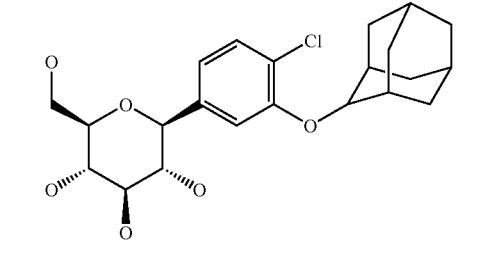 |
| (55) | 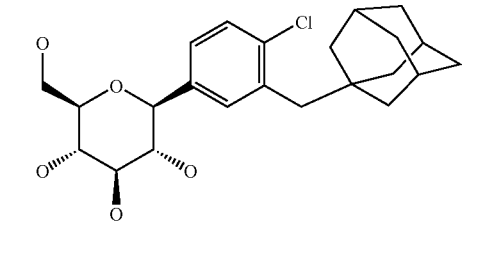 |
| (56) | 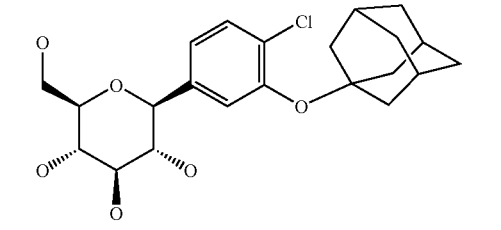 |

| Ex. | Structure |
|---|---|
| (57) | 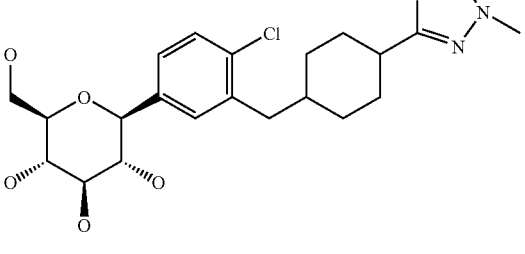 |
| (58) | 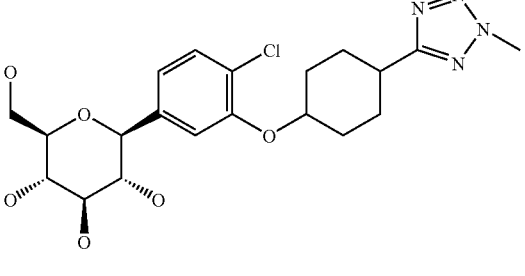 |
| (59) | 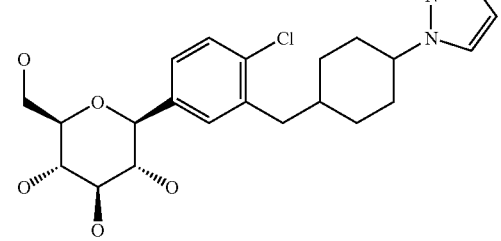 |
| (60) | 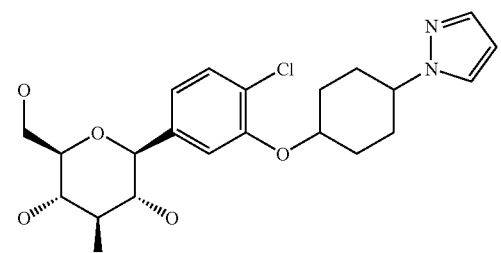 |

The following are examples of formulations in which the phrase "active substance" denotes one or more compounds according to the invention, including the salts thereof. In the case of one of the combinations with one or more other active substances the term "active substance" also includes the additional active substances.

EXAMPLE A

Tablets Containing 100 mg of Active Substance

Composition:
    1 tablet contains:

| | |
|---|---|
| active substance | 100.0 mg |
| lactose | 80.0 mg |

-continued

|   |   |
|---|---|
| corn starch | 34.0 mg |
| polyvinylpyrrolidone | 4.0 mg |
| magnesium stearate | 2.0 mg |
|  | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 mg of Active Substance

Composition:

1 tablet contains:

|   |   |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
|  | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

Hard Gelatine Capsules Containing 150 mg of Active Substance 1 capsule contains:

|   |   |
|---|---|
| active substance | 150.0 mg |
| corn starch (dried | approx. 180.0 mg |
| lactose (powdered) | approx. 87.0 mg |
| magnesium stearate | 3.0 mg |
|  | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

Suppositories Containing 150 mg of Active Substance 1 suppository contains:

|   |   |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
|  | 2,000.0 mg |

Preparation:

After the suppository mass has been melted the active substance is homogeneously distributed therein and the melt is poured into chilled moulds.

EXAMPLE E

Ampoules Containing 10 mg Active Substance

Composition:

|   |   |
|---|---|
| active substance | 10.0 mg |
| 0.01 N hydrochloric acid q.s. |  |
| double-distilled water ad | 2.0 ml |

Preparation:

The active substance is dissolved in the necessary amount of 0.01 N HCl, made isotonic with common salt, filtered sterile and transferred into 2 ml ampoules.

EXAMPLE F

Ampoules Containing 50 mg of Active Substance

Composition:

|   |   |
|---|---|
| active substance | 50.0 mg |
| 0.01 N hydrochloric acid q.s. |  |
| double-distilled water ad | 10.0 ml |

Preparation:

The active substance is dissolved in the necessary amount of 0.01 N HCl, made isotonic with common salt, filtered sterile and transferred into 10 ml ampoules.

What is claimed is:

1. A D-Glucopyranosyl-phenyl-substituted compound of formula I

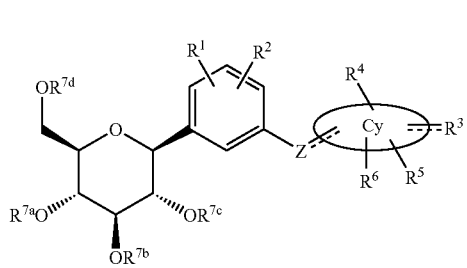

wherein

---- denotes a single or double bond, and

Cy denotes a 5- or 6-membered saturated or monounsaturated carbocycle, which may comprise one, two or three heteroatoms selected independently of one another from N, O and S, and which is substituted by $R^4$, $R^5$ and $R^6$ through a single bond and by $R^3$ through a single or double bond, and wherein one or two methylene groups may be replaced by CO or a sulphanyl group may be replaced by SO or $SO_2$, and wherein one or more H atoms bound to carbon may be replaced by fluorine, Z denotes —O—, —$CH_2$—, —CH=, —$NR^N$—, —CO—, —S—, —SO— or —$SO_2$—, while H atoms of the methylene or methanylylidene bridge may be substituted independently of one another by $CH_3$ or F;

$R^1$ denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, $C_{1-4}$-alkoxycarbonyl, amino, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, $C_{1-6}$-alkyloxy, $C_{3-7}$-cycloalkyloxy, $C_{5-7}$-cycloalkenyloxy, aryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, and $R^2$ denotes hydrogen, fluorine, chlorine, bromine, hydroxy, $C_{1-4}$-alkyl, $C_{1-4}$-alkoxy, cyano or nitro, while alkyl groups may be mono- or polysubstituted by fluorine, or in the event that $R^1$ and $R^2$ are bound to two adjacent C atoms of the phenyl ring, $R^1$ and $R^2$ may be joined together such that $R^1$ and $R^2$ together form a $C_{3-5}$-alkylene, $C_{3-5}$-alkenylene or butadienylene bridge, which may be partly or completely fluorinated or may be mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and wherein in the case of a butadienylene bridge one or two methyne groups may be replaced by an N atom, $R^3$ denotes hydrogen, fluorine, chlorine, bromine, $C_{1-6}$-alkyl, $C_{2-6}$-alkynyl, $C_{2-6}$-alkenyl, $C_{3-7}$-cycloalkyl, $C_{3-7}$-cycloalkyl-$C_{1-3}$-alkyl, $C_{5-7}$-cycloalkenyl, $C_{5-7}$-cycloalkenyl-$C_{1-3}$-alkyl, aryl, heteroaryl, aryl-$C_{1-3}$-alkyl, heteroaryl-$C_{1-3}$-alkyl, $C_{1-4}$-alkylcarbonyl, arylcarbonyl, heteroarylcarbonyl, aminocarbonyl, $C_{1-4}$-alkylaminocarbonyl, di-($C_{1-3}$-alkyl)amino-carbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)piperazin-1-ylcarbonyl, hydroxycarbonyl, $C_{1-4}$-alkoxycarbonyl, $C_{1-4}$-alkylamino, di-($C_{1-3}$-alkyl)amino, pyrrolidin-1-yl, piperidin-1-yl, morpholin-4-yl, piperazin-1-yl, 4-($C_{1-4}$-alkyl)piperazin-1-yl, $C_{1-4}$-alkylcarbonylamino, arylcarbonylamino, heteroarylcarbonylamino, $C_{1-4}$-alkylsulphonylamino, arylsulphonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphinyl, $C_{1-4}$-alkylsulphonyl, $C_{3-7}$-cycloalkylsulphanyl, $C_{3-7}$-cycloalkylsulphinyl, $C_{3-7}$-cycloalkylsulphonyl, $C_{5-7}$-cycloalkenylsulphanyl, $C_{5-7}$-cycloalkenylsulphinyl, $C_{5-7}$-cycloalkenylsulphonyl, arylsulphanyl, arylsulphinyl, arylsulphonyl, amino, hydroxy, cyano or nitro, while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and in cycloalkyl and cycloalkenyl groups one or two methylene groups may be replaced independently of one another by O, S, CO, SO or $SO_2$, and in N-heterocycloalkyl groups a methylene group may be replaced by CO or $SO_2$, or $R^3$ denotes a group Y attached to Cy by a double bond, $R^4$ denotes hydrogen, fluorine, chlorine, cyano, nitro, amino, $C_{1-3}$-alkyl-amino, di-($C_{1-3}$-alkyl)amino, $C_{1-3}$-alkylcarbonylamino, $C_{1-3}$-alkyl, $C_{1-3}$-alkoxy, hydroxycarbonyl, $C_{1-3}$-alkoxycarbonyl or methyl or methoxy substituted by 1 to 3 fluorine atoms, or in the event that $R^3$ and $R^4$ are bound to the same C atom of the Cy ring, $R^3$ and $R^4$ may be joined together such that $R^3$ and $R^4$ together form a $C_{2-6}$-alkylene or $C_{4-6}$-alkenylene bridge, which may be partly or completely fluorinated or may be mono- or disubstituted by identical or different substituents selected from chlorine, hydroxy, $C_{1-3}$-alkoxy and $C_{1-3}$-alkyl and wherein one or two methylene groups may be replaced independently of one another by O, S, CO, SO, $SO_2$ or $NR^N$, or in the event that $R^3$ and $R^4$ are bound to two adjacent atoms of the Cy ring, $R^3$ and $R^4$ may be joined together such that $R^3$ and $R^4$ together with the two adjacent atoms of the Cy ring form an anellated saturated or mono- or polyunsaturated 5- or 6-membered carbocycle, wherein one or two methylene groups may be replaced independently of one another by O, S, CO, SO, $SO_2$ or $NR^N$ and/or one or two methyne groups may be replaced by N, and which may be mono- or polyfluorinated or mono- or disubstituted by identical or different substituents selected from chlorine, hydroxy, $C_{1-3}$-alkoxy and $C_{1-3}$-alkyl or in the case of an aromatic anellated ring may be mono- or disubstituted by identical or different substituents L, $R^5$ denotes hydrogen, fluorine, chlorine, cyano, $C_{1-3}$-alkyl, $C_{1-3}$-alkoxy or methyl or methoxy substituted by 1 to 3 fluorine atoms, or $R^4$ and $R^5$ are attached to one another such that $R^4$ and $R^5$ together form a $C_{1-4}$-alkylene or $C_{2-4}$-alkenylene bridge, which together with 2, 3 or 4 atoms of the Cy ring forms an anellated or bridged cycle and which may be partly or completely fluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, S, CO, SO, $SO_2$ or $NR^N$, and $R^6$ denotes hydrogen, $C_{1-3}$-alkyl or fluorine, or $R^4$, $R^5$ and $R^6$ are attached to one another such that $R^4$, $R^5$ and $R^6$ together form a $C_{3-6}$-alkanetriyl bridge, which together with the Cy ring forms a bridged bicyclic or tricyclic system, while the alkanetriyl bridge may be mono- or polyfluorinated or mono- or disubstituted by identical or different substituents selected from chlorine, hydroxy, $C_{1-3}$-alkoxy and $C_{1-3}$-alkyl, and wherein one or two methylene groups may be replaced independently of one another by O, CO, $SO_2$ or $NR^N$, and Y denotes oxygen, or methylidene, fluoromethylidene, chloromethylidene, $C_{1-6}$-alkyl-methylidene, $C_{2-6}$-alkenyl-methylidene, $C_{2-6}$-alkynyl-methylidene, $C_{3-7}$-cycloalkyl-methylidene, $C_{5-7}$-cycloalkenyl-methylidene, $C_{3-7}$-cycloalkylidene, $C_{5-7}$-cycloalkenylidene, $C_{3-7}$-cycloalkyl-$C_{1-3}$-alkyl-methylidene, $C_{5-7}$-cycloalkenyl-$C_{1-3}$-alkyl-methylidene, arylmethylidene, heteroarylmethylidene, aryl-$C_{1-}$-alkyl-methylidene or heteroaryl-$C_{1-3}$-alkyl-methylidene, while alkyl, alkenyl, alkynyl, cycloalkyl, cycloalkenyl, cycloalkylidene and cycloalkenylidene groups may be partly or completely fluorinated or mono- or disubstituted by identical or different substituents selected from chlorine, cyano, hydroxy, $C_{1-3}$-alkoxy, $C_{1-4}$-alkylsulphanyl and $C_{1-4}$-alkyl, and the above-mentioned unsubstituted methylidene group or the above-mentioned monosubstituted methylidene groups may additionally be monosubstituted by fluorine, chlorine, $C_{1-3}$-alkyl, trifluoromethyl, $C_{1-4}$-alkoxy, cyano or nitro, and in cycloalkyl, cycloalkenyl, cycloalkylidene and cycloalkenylidene groups one or two methylene groups may be replaced independentiy of one another by O, S, CO, SO, $SO_2$ or $NR^N$, or Y denotes a group according to partial formula

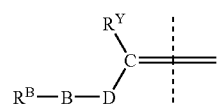

wherein

D denotes carbonyl or sulphonyl, $R^Y$ denotes hydrogen, fluorine, chlorine, cyano, trifluoromethyl or $C_{1-4}$-alkyl, B denotes a single bond, —O— or —$NR^N$—, $R^B$ denotes hydrogen, $C_{1-6}$-alkyl, $C_{3-6}$-alkenyl, $C_{3-6}$-alkynyl, $C_{3-7}$-cycloalkyl, $C_{5-7}$-cycloalkenyl, $C_{3-7}$-cycloalkyl-$C_{1-3}$-alkyl, $C_{5-7}$-cycloalkenyl-$C_{1-3}$-alkyl, aryl, heteroaryl, aryl-$C_{1-3}$-alkyl or heteroaryl-$C_{1-3}$-alkyl, while alkyl, cycloalkyl and cycloalkenyl groups may be partly or completely fluorinated or may be mono- or disubstituted by identical or different substituents selected from chlorine, cyano, hydroxy, $C_{1-3}$-alkoxy and $C_{1-3}$-alkyl, or $R^B$ and B are joined together to form a heterocyclic ring selected from pyrrolidine, morpholine, piperidine, piperazine and 4-($C_{1-4}$-alkyl)-piperazine, while the heterocyclic ring is bound to the group D via the imino group, $R^N$ independently of one another denote H or $C_{1-4}$-alkyl, L selected independently of one another from among fluorine, chlorine, bromine, iodine, $C_{1-3}$-alkyl, difluoromethyl, trifluoromethyl, $C_{1-3}$-alkoxy, difluoromethoxy, trifluoromethoxy and cyano, $R^{7a}$, $R^{7b}$, $R^{7c}$, $R^{7d}$ independently of one another have a meaning selected from among hydrogen, ($C_{1-18}$-alkyl)carbonyl, ($C_{1-18}$-alkyl)oxycarbonyl, arylcarbonyl and aryl-($C_{1-3}$-alkyl)-carbonyl, while by the aryl groups mentioned in the definition of the above groups are meant phenyl or naphthyl groups, which may be mono- or disubstituted independently of one another by identical or different groups L; and by the heteroaryl groups mentioned in the definition of the above-mentioned groups is meant a pyrrolyl, furanyl, thienyl, imidazolyl, pyridyl, indolyl, benzofuranyl, benzothiophenyl, quinolinyl or isoquinolinyl group, or a pyrrolyl, furanyl, thienyl, imidazolyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted independently of one another by identical or different groups L;

while by the N-heterocycloalkyl group mentioned in the definition of the above-mentioned groups is meant a saturated carbocyclic ring which comprises an imino group in the ring, which may comprise another optionally substituted imino group or an O or S atom in the ring, and unless otherwise stated, the above-mentioned alkyl groups may be straight-chain or branched, the tautomers, their stereoisomers, the mixtures thereof and the salts thereof, particularly the physiologically acceptable salts thereof, but excluding the following compounds:

3-[(3-β-D-glucopyranosyl-4,5-dimethoxyphenyl)methyl]-4-[(3,4-dimethoxyphenyl)methyl]-dihydro-2(3H)-furanone;

3-[(3-β-D-glucopyranosyl-4-hydroxy-5-methoxyphenyl)methyl]-4-[(3,4-dimethoxyphenyl)methyl]-dihydro-3-methyl-(3H)-furanone; and 3-[(3-β-D-glucopyranosyl-4-hydroxy-5-methoxyphenyl)methyl]-4-[(3-methoxy-4-hydroxyphenyl)methyl]-dihydro-2(3H)-furanone.

2. A D-Glucopyranosyl-phenyl-substituted compound according to claim 1, wherein the Cy ring denotes cyclopentane, cyclohexane, pyrrolidine, piperidine, piperazine, morpholine, tetrahydrofuran, tetrahydropyran, 1,3-dioxane, 1,4-dioxane, tetrahydrothiophene, dithiolan or 1,3-dithiane, wherein a methylene group may be replaced by CO, and which is substituted as specified in claim 1 with $R^3$, $R^4$, $R^5$ and $R^6$, and wherein additionally one or more H atoms bound to carbon may be replaced by fluorine.

3. A D-Glucopyranosyl-phenyl-substituted compound according to claim 1, which is of the formula I.1 or I.1'

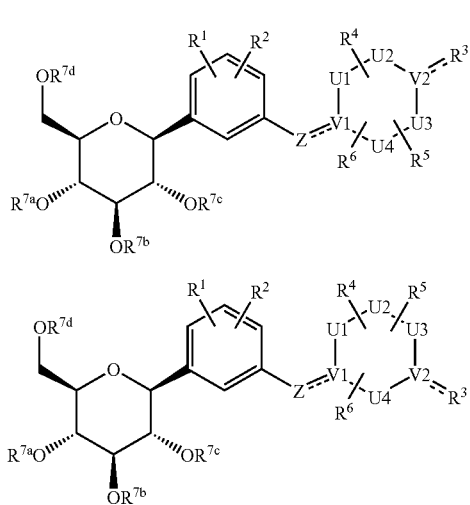

wherein
V1, V2 independently of one another represent C or N,
U1, U2, U3, U4 independently of one another represent C, N, O, CO or $SO_2$,
with the proviso that in the ring formed by U and V there are a maximum of 2 heteroatoms selected from N and O, which are not directly joined together, and there is a maximum of one group selected from CO and $SO_2$, and remaining free chemical bonds to C and N atoms are saturated with hydrogen; and
wherein $R^1$ to $R^6$, Z, $R^{7a}$, $R^{7b}$, $R^{7c}$, $R^{7d}$ have the meanings according to claim 1.

4. A D-Glucopyranosyl-phenyl-substituted compound according to claim 1, which is of the formula I.2

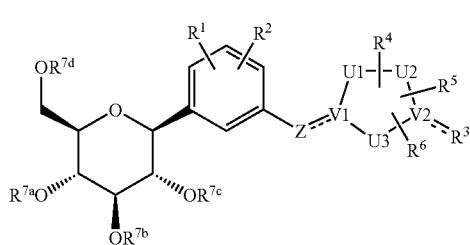

wherein
V1, V2 independently of one another represent C or N,
U1, U2, U3 independently of one another represent C, N, O, CO or $SO_2$,
with the proviso that in the ring formed by U and V there are a maximum of 2 heteroatoms selected from N and O, which are not directly joined together, and a maximum of one group selected from CO and $SO_2$, and remaining free chemical bonds to C and N atoms are saturated with hydrogen; and
wherein $R^1$ to $R^6$, Z, $R^{7a}$, $R^{7b}$, $R^{7c}$, $R^{7d}$ have the meanings according to claim 1.

5. A D-Glucopyranosyl-phenyl-substituted compound according to claim 1, wherein:
$R^1$ denotes hydrogen, fluorine, chlorine, bromine, iodine, $C_{1-6}$-alkyl, $C_{2-6}$-alkynyl, $C_{2-6}$-alkenyl, $C_{3-7}$-cycloalkyl, $C_{5-7}$-cycloalkenyl, $C_{1-6}$-alkyloxy, $C_{3-7}$-cycloalkyloxy or cyano, while in cycloalkyl and cycloalkenyl groups one or two methylene units may be replaced independently of one another by O or CO and alkyl, alkenyl and alkynyl groups may be partly or completely fluorinated.

6. A D-Glucopyranosyl-phenyl-substituted compound according to claim 1, wherein:
$R^2$ denotes hydrogen, fluorine, chlorine, bromine, methyl, hydroxy, methoxy, ethoxy, trifluoromethoxy, cyano, nitro or methyl substituted by 1 to 3 fluorine atoms.

7. A D-Glucopyranosyl-phenyl-substituted compound according to claim 1, wherein:
$R^3$ denotes hydrogen, fluorine, chlorine, $C_{1-6}$-alkyl, $C_{2-6}$-alkynyl, $C_{2-6}$-alkenyl, $C_{3-7}$-cycloalkyl, $C_{3-7}$-cycloalkyl-methyl, $C_{5-7}$-cycloalkenyl, $C_{3-7}$-cycloalkenyl-methyl, aryl, heteroaryl, $C_{1-4}$-alkylcarbonyl, aminocarbonyl, $C_{1-4}$-alkylaminocarbonyl, di-($C_{1-3}$-alkyl)aminocarbonyl, $C_{1-4}$-alkoxycarbonyl, di-($C_{1-3}$-alkyl)amino, pyrrolidin-1-yl, piperidin-1-yl, morpholin-4-yl, $C_{1-4}$-alkylcarbonylamino, $C_{1-6}$-alkoxy, $C_{3-7}$-cycloalkyloxy, $C_{5-7}$-cycloalkenyloxy, aryloxy, heteroaryloxy, $C_{1-4}$-alkylsulphanyl, $C_{1-4}$-alkylsulphonyl, $C_{3-7}$-cycloalkylsulphanyl, $C_{3-7}$-cycloalkylsulphonyl, $C_{5-7}$-cycloalkenylsulphanyl, $C_{5-7}$-cycloalkenylsulphonyl, hydroxy or cyano, and
in the event that $R^3$ is bound to an N atom, $R^3$ denotes hydrogen, cyano, $C_{1-4}$-alkyl, $C_{2-6}$-alkynyl, $C_{2-6}$-alkenyl, $C_{3-6}$-cycloalkyl, $C_{3-6}$-cycloalkyl-$C_{1-3}$-alkyl, $C_{5-6}$-cycloalkenyl, $C_{5-6}$-cycloalkenyl-$C_{1-3}$-alkyl, aryl, heteroaryl, aryl-$C_{1-3}$-alkyl, heteroaryl-$C_{1-3}$-alkyl, $C_{1-4}$-alkylcarbonyl, arylcarbonyl, heteroarylcarbonyl, $C_{1-4}$-alkylsulphonyl, arylsulphonyl or heteroarylsulphonyl,
while alkyl, alkenyl, alkynyl, cycloalkyl and cycloalkenyl groups may be partly or completely fluorinated or may be mono- or disubstituted by identical or different substituents selected from chlorine, hydroxy, $C_{1-3}$-alkoxy and $C_{1-3}$-alkyl, and
in cycloalkyl and cycloalkenyl groups one or two methylene groups may be replaced independently of one another by O, S, CO, SO or $SO_2$, and
in N-heterocycloalkyl groups a methylene group may be replaced by CO or $SO_2$,
while the terms aryl and heteroaryl are defined according to claim 1 and aryl and heteroaryl groups may be mono- or disubstituted independently of one another by identical or different groups L, and L is defined according to claim 1.

8. A D-Glucopyranosyl-phenyl-substituted compound according to claim 1, wherein:
$R^3$ is bound to Cy by a double bond and denotes oxygen, $C_{1-6}$-alkyl-methylidene, $C_{2-6}$-alkynyl-methylidene, $C_{2-6}$-alkenyl-methylidene, $C_{3-7}$-cycloalkyl-methylidene or $C_{3-7}$-cycloalkylidene,
while the above-mentioned alkyl, alkenyl and alkynyl groups may be partly or completely fluorinated and may be mono- or disubstituted independently of one another by substituents selected from chlorine, hydroxy, $C_{1-3}$-alkoxy and $C_{1-3}$-alkyl, and the above-mentioned unsubstituted methylidene group or the above-mentioned monosubstituted methylidene groups may additionally be monosubstituted by fluorine, $C_{1-3}$-alkyl, trifluoromethyl or cyano, and in a cycloalkylidene group a methylene group may be replaced by O, S or $NR^N$ or an ethylene group may be replaced by $-NR^N-CO-$, $-CO-NR^N-$, $-O-CO-$ or $-CO-O-$ or Y denotes a group according to partial formula T

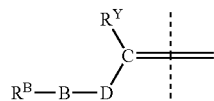

wherein
$R^Y$ denotes hydrogen, fluorine, cyano, trifluoromethyl or $C_{1-3}$-alkyl,
D denotes carbonyl or sulphonyl,
B denotes a single bond, $-O-$ or $-NR^N-$,
$R^B$ denotes $C_{1-6}$-alkyl, $C_{3-7}$-cycloalkyl, $C_{5-7}$-cycloalkenyl, $C_{3-7}$-cycloalkyl-$C_{1-3}$-alkyl, $C_{5-7}$-cycloalkenyl-$C_{1-3}$-alkyl, aryl, heteroaryl, aryl-$C_{1-3}$-alkyl or heteroaryl-$C_{1-3}$-alkyl-,
while alkyl, cycloalkyl and cycloalkenyl groups may be partly or completely fluorinated or may be mono- or disubstituted by identical or different substituents selected from cyano, hydroxy, $C_{1-3}$-alkoxy and $C_{1-3}$-alkyl, or
$R^B$ and B are joined together to form a heterocyclic ring selected from pyrrolidine, morpholine, piperidine, piperazine and 4-($C_{1-4}$-alkyl)-piperazine, while the heterocyclic ring is bound to the group D via the imino group and
$R^N$ is defined as in claim 1.

9. A D-Glucopyranosyl-phenyl-substituted compound according to claim 1, wherein:
$R^4$, $R^5$ and $R^6$ independently of one another represent hydrogen, fluorine or methyl.

10. A D-Glucopyranosyl-phenyl-substituted compound according to claim 1, wherein:
the groups $R^4$, $R^5$ and $R^6$ are joined together to form a $C_{4-5}$-alkanetriyl bridge and together with the Cy ring form a tricyclic system selected from tricyclononane, tricyclodecane and tricycloundecane, which is unsubstituted or may be mono- or polyfluorinated or mono- or disubstituted by identical or different substituents selected from chlorine, hydroxy, $C_{1-3}$-alkoxy and $C_{1-3}$-alkyl.

11. A D-Glucopyranosyl-phenyl-substituted compound according to claim 1, wherein:
Z denotes $-O-$, $-CH_2-$, $-CF_2-$, $-C(CH_3)_2-$, $-CH=$, $-NR^N-$ or $-CO-$.

12. A D-Glucopyranosyl-phenyl-substituted compound according to claim 1, wherein:
$R^{7a}$, $R^{7b}$, $R^{7c}$, $R^{7d}$ independently of one another represent hydrogen, ($C_{1-6}$-alkyl)oxycarbonyl, ($C_{1-8}$-alkyl)carbonyl or benzoyl, preferably hydrogen.

13. A physiologically acceptable salt of a compound according to claim 1 with an inorganic or organic acid.

14. A method of treating diseases or conditions influenced by inhibiting the sodium-dependent glucose cotransporter SGLT, wherein the disease or condition is selected from the group consisting of diabetes, complications of diabetes and reactive hypoglycaemia, said method comprised of the steps of administering to a patient in need thereof a therapeutically effective amount of compound according to claim 1 or a physiologically acceptable salt thereof.

15. A process for preparing a pharmaceutical composition comprising a compound according to claim 1, wherein said compound is incorporated in one or more inert carriers and/or diluents by a non-chemical method.

16. The method of claim 14, wherein the disease or condition is selected from the group consisting of type 1 and/or type 2 diabetes mellitus.

17. A D-Glucopyranosyl-phenyl-substituted compound according to claim 10, wherein:
the groups $R^4$, $R^5$ and $R^6$ are joined together to form a $C_{4-5}$-alkanetriyl bridge and together with the Cy ring form a tricyclic adamantine system, which is unsubstituted or may be mono- or polyfluorinated or mono- or disubstituted by identical or different substituents selected from chlorine, hydroxy, $C_{1-3}$-alkoxy and $C_{1-3}$-alkyl.

* * * * *